United States Patent [19]
Pachuk et al.

[11] Patent Number: 6,143,527
[45] Date of Patent: *Nov. 7, 2000

[54] CHAIN REACTION CLONING USING A BRIDGING OLIGONUCLEOTIDE AND DNA LIGASE

[75] Inventors: Catherine J. Pachuk, Lansdowne; Manoj Samuel, West Chester; C. Satishchandran, Lansdale, all of Pa.

[73] Assignee: American Home Products Corporation, Madison, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/852,268

[22] Filed: May 6, 1997

Related U.S. Application Data

[63] Continuation-in-part of application No. 08/642,045, May 6, 1996.

[51] Int. Cl.[7] .............................. C12P 19/34; C07H 21/04
[52] U.S. Cl. ...................... 435/91.1; 435/91.2; 435/91.4; 435/91.5; 435/91.52; 536/25.3
[58] Field of Search ................................. 435/91.1, 91.2, 435/91.4, 91.5, 91.52; 536/25.3

[56] References Cited

U.S. PATENT DOCUMENTS

| | | | |
|---|---|---|---|
| 4,703,011 | 10/1987 | Kit et al. | 435/236 |
| 4,945,050 | 7/1990 | Sanford et al. | 435/172.1 |
| 5,036,006 | 7/1991 | Sanford et al. | 435/170.1 |
| 5,270,163 | 12/1993 | Gold et al. | 435/6 |
| 5,403,709 | 4/1995 | Agrawal et al. | 435/6 |
| 5,470,722 | 11/1995 | Jones | 435/91.2 |
| 5,525,470 | 6/1996 | Cohen et al. | 435/6 |
| 5,648,245 | 7/1997 | Fire et al. | 435/91.1 |

FOREIGN PATENT DOCUMENTS

| | | |
|---|---|---|
| WO 90/11092 | 10/1992 | WIPO . |
| WO 93/17706 | 9/1993 | WIPO . |
| WO 93/23552 | 11/1993 | WIPO . |
| WO 94/16737 | 8/1994 | WIPO . |

OTHER PUBLICATIONS

Pachuk et al., FASEB J. 10(6), A1127 (abstract)(1996).
Jones et al., BioTechniques 15(5), 894–904 (1993).
Holmes, D. et al., "Cloning of an Aminoglycoside–Resistance–Encoding Gene, kamC, from *Saccharopolyspora hirsuta*: Comparison with kamB from *Streptomyces tenebrarius*", *Gene*, 1991, 102, 19–26.
Kües, U. and Stahl, "Replication of Plasmids in Gram–Negative Bacteria", *Microbiological Reviews*, 1989, 53(4), 491–516.

(List continued on next page.)

*Primary Examiner*—Kenneth R. Horlick
*Attorney, Agent, or Firm*—Howson and Howson

[57] ABSTRACT

Chain reaction cloning methods and reagents and kits for performing such methods are provided. Chain reaction cloning allows ligation of double-stranded DNA molecules by DNA ligases and bridging oligonucleotides. Double-stranded nucleic acid molecules are denatured into single-stranded molecules. The ends of the molecules are brought together by hybridization to a template. The template ensures that the two single-stranded nucleic acid molecules are aligned correctly. DNA ligase joins the two nucleic acid molecules into a single, larger, composite nucleic acid molecule. The nucleic acid molecules are subsequently denatured so that the composite molecule formed by the ligated nucleic acid molecules and the template cease to hybridize to each. Each composite molecule then serves as a template for orienting unligated, single-stranded nucleic acid molecules. After several cycles, composite nucleic acid molecules are generated from smaller nucleic acid molecules. A number of applications are disclosed for chain reaction cloning including site-specific ligation of DNA fragments generated by restriction enzyme digestion, DNAse digestion, chemical cleavage, enzymatic or chemical synthesis, and PCR amplification.

19 Claims, 21 Drawing Sheets

OTHER PUBLICATIONS

Matsumura, M. et al., "Enzymatic and Nucleotide Sequence Studies of a Kanamycin–Inactivating Enzyme Encoded by a Plasmid from Thermophilic Bacilli in Comparison with That Encoded by Plasmid pUB110", *J. Bacteriol.*, 1984, 160(1), 413–420.

Oka, A. et al., "Nucleotide Sequence of the Kanamycin Resistance Transposon Tn903", *J. Mol. Biol.*, 1981, 147, 217–226.

Sadaie, Y. et al., "Purification and Characterization of a Kanamycin Nucleotidyltransferase from Plasmid pUB110–Carrying Cells of *Bacillus subtilis*", *J. Bateriol.*, 1980, 141(3), 1178–1182.

Satishchandran, C. et al., "Novel *Escherichia coli* K–12 Mutants Impaired in S–Adenosylmethionine Synthesis", *J. Bacteriol.*, 1990, 172(8), 4489–4496.

Schwotzer, U. et al., "R–Plasmid Mediated Aminoglycoside Resistance in *Staphylococcus epidermidis*: Structure Determination of the Products of an Enzyme Nucleotidylating the 4'–and 4"–Hydroxyl Group of Aminoglycoside Antibiotics", *FEMS Microbiology Letters*, 1978, 3, 29–33.

Shaw, K.J. et al., "Correlation between Aminoglycoside Resistance Profiles and DNA Hybridization of Clinical Isolates", *Antimicrobial Agents and Chemotherapy*, 1991, 35 (11), 2253–2261.

Shaw, K.J. et al., "Molecular Genetics of Aminoglycoside Resistance Genes and Familial Relationships of the Aminoglycoside–Modifying Enzymes", *Microbiol. Reviews*, 1993, 57 (1), 138–163.

Siregar, J. et al., "Purification, Characterization, and Investigation of the Mechanism of Aminoglycoside 3'–Phosphotransferase Type Ia", *Biochem.*, 1995, 34, 12681–12688.

Wingard, Jr. L. et al., "Inhibitors of Bacterial Ribosomal Actions", Chap. 47 in "Human Pharmacology Molecular–to–Clinical", Mosby Year Book, St. Louis, 1991, 659–676.

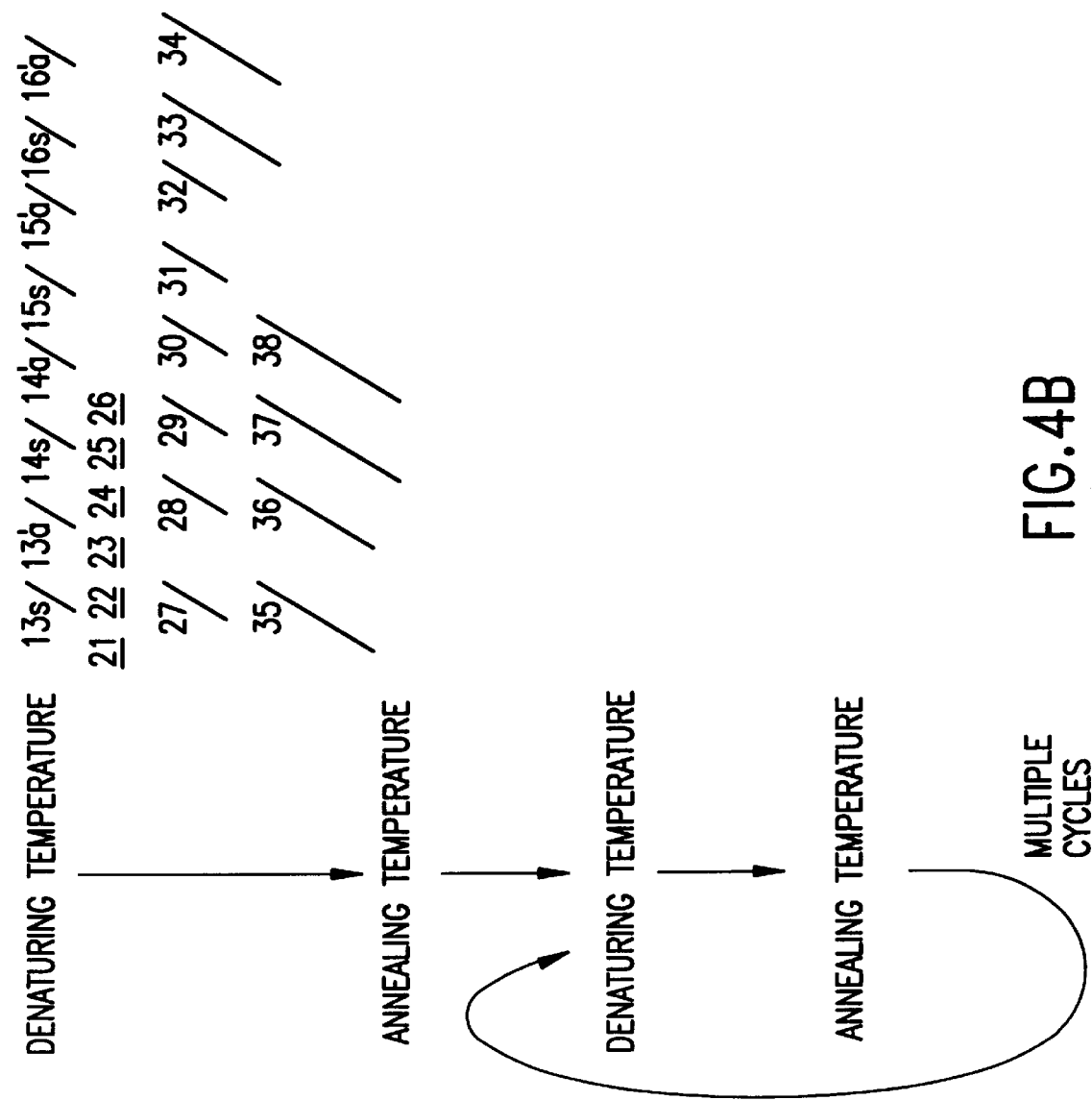

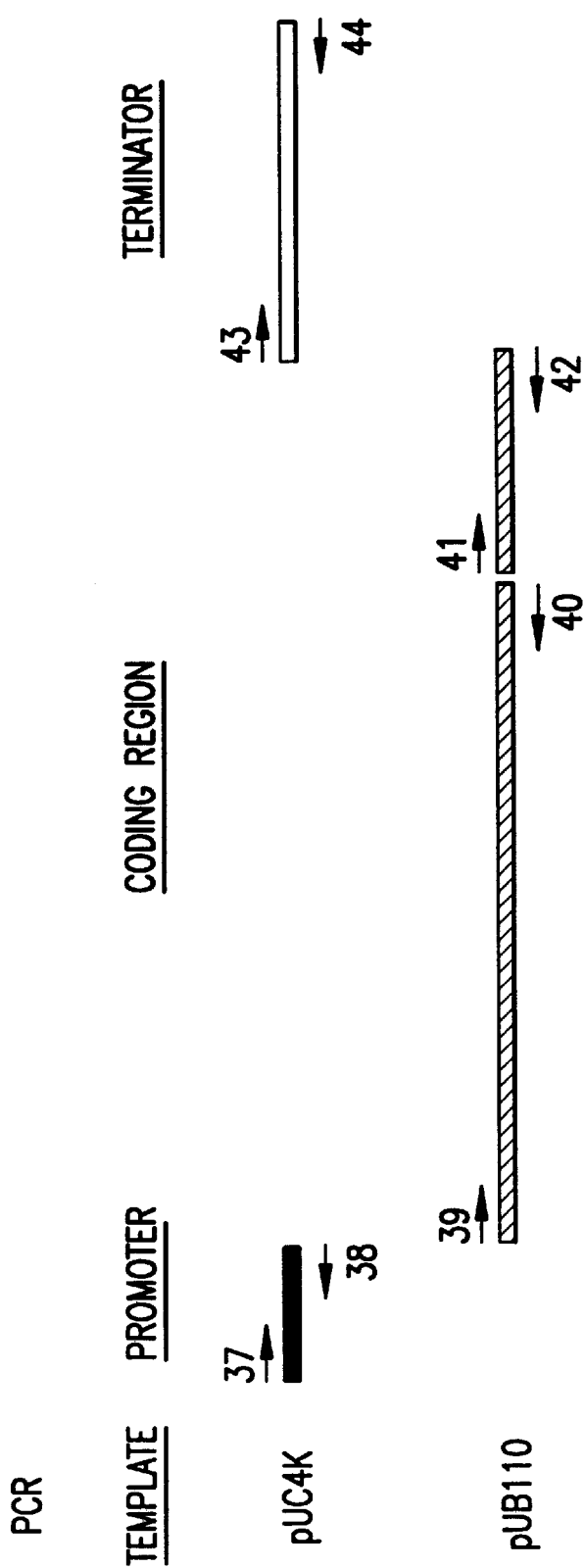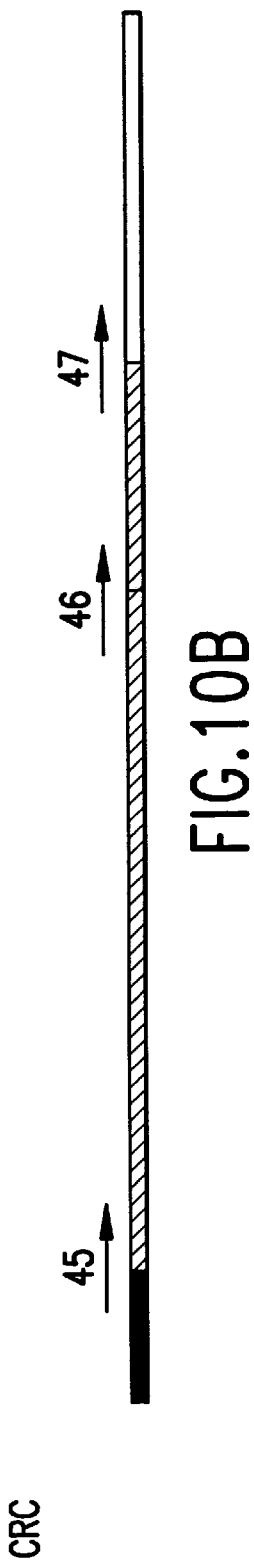
FIG.10A
FIG.10B

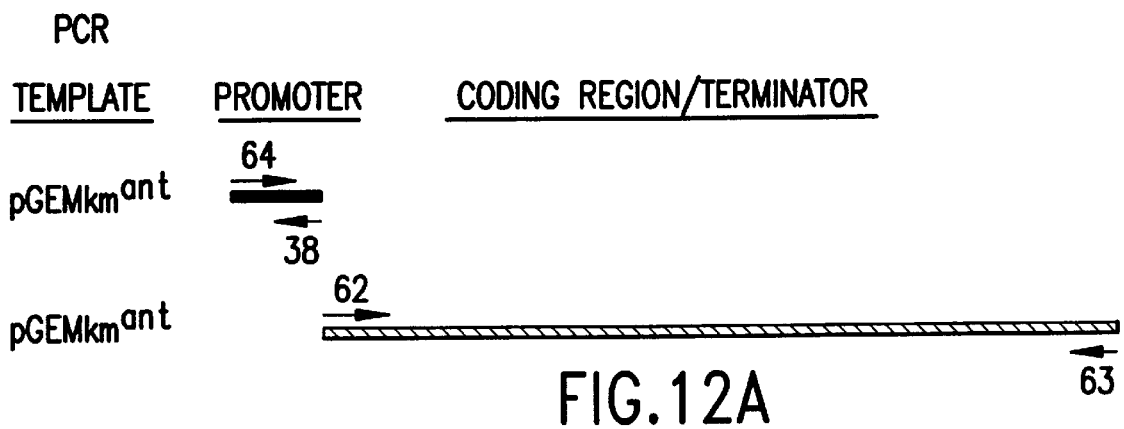
FIG.11
FIG.12A
FIG.12B

MPV 64
```
         20            40            60            80           100
GCTCTAGAGGGCCGGCCGGGGAAAGCCACGTTGTGTCTCAAATCTCTGATGTTACATTGCACAAGATAAAAATATATCATGAACAATAAAACTGTCT
CGAGATCTCCGGCCGGCCCCTTTCGGTGCAACACAGAGTTTTAGAGACTACAATGTAACGTGTTCTATTTTTATATAGTAGTACTTGTTATTTTGACAGA
        MPV 37
        120           140           160           180           200
GCTTACATAAACAGTAATACAAGGGGTGTTATGAACGGACCAATAATAACTAGAGAAGAAGAATGAAGATTGTTCATGAAATTAAGGAACGAATAT
CGAATGTATTTGTCATTATGTTCCCCACAATACTTGCCTGGTTATTATTATTACTGATCTCTTCTTTCTTACTTCTAACAAGTACTTAATTCCTTGCTTATA
        MPV 38                                                              MPV 62
        220           240           260           280           300
GCTTACATAAACAGTAATACAAGGGGTGTTATGAACGGACCAATAATAACTAGAGAAGAAGAATGAAGATTGTTCATGAAATTAAGGAACGAATAT
CGAATGTATTTGTCATTATGTTCCCCACAATACTTGCCTGGTTATTATTATTACTGATCTCTTCTTTCTTACTTCTAACAAGTACTTAATTCCTTGCTTATA
        MPV 38
        220           240           260           280           300
TGGATAAATATGGGACCCGCTTAAGGCTATTGAGATGATGTTAACAATTCCGATAACTACCGGAGAACTCTACTACACACAGTA
ACCTATTTATACCCTGGCGAATTGTCTACAATGTTAAGGCTATACTGACTGCCTATATTCGAGATATTGAGATGATGTGTCAT
        320           340           360           380           400
GTCAACAGAGGAAGCAGAGTTCAGCTCAAGTCGGTCTCCTTCGTCTTCAAGTCGGTACTTACCTGTTGGCCACTCACCTTCCACTATCGCTTCTCACTTAAAACTATCGCTTCTCACTTAAAACTATCGCTTCTCAC
CAGTTGTCTCCTTCGTCTTCAAGTCGGTCTCCTTCGTCTTCAAGTCGGTACTTACCTGTTGGCCACTCACCTTCCACTATCGCTTCTCACTTAAAACTATCGCTTCTCACTTAAAACTATCGCTTCTCAC
        420           440           460           480           500
CAGGTGGAATCAGATTGGCCGCTTACACATGGTCAATTTTCTATTTTGCCGATTTATGATTCAGGTGGATACTTAGAGAAAGTGTATCAAACTGCTA
GTCCACCTTAGTCTAACCGGCTAAATGTGTACCAGTTAAAAGAGATAAAACGGCTAAATACTAAGTCCACCTATGAATCTCTTTCACATAGTTTGACGAT
        520           540           560           580           600
AATCGGTAGAAGCCCAAACGTTCCACGATGCGATTTGTGCCCTTATCGTAGAAGAGCTGTTTGAATATGCAGGCAAATGGGTAATATTCGTGTGCAAGG
TTAGCCATCTTCGGGTTTGCAAGGTGCTACGCTAAACACGGAATAGCATCTTCTCGACAACTTATACGTCCGTTACCGATTATATAAGCACACGTTCC
        620           640           660           680           700
ACCGACAACATTTCTACCATCCTTGACTGTACAGGTAGCAATGGCAGGTGCCATGTCTTGATTGGTCTGCATCATCGACGACGACGAGCGCGTCG
TGGCTGTTGTAAAGATGGTAGGAACTGACATGTCCATGTTACCGTCCACGGTACAACTAACCAGACGTAGTAGCACAATATGCTGCTCGCGCAGC
                                                                          MPV 40
```

CHAIN REACTION CLONING USING A BRIDGING OLIGONUCLEOTIDE AND DNA LIGASE

CROSS REFERENCE TO RELATED APPLICATIONS

This application is a continuation in part application of Ser. No. 08/642,045 filed May 6, 1996.

FIELD OF THE INVENTION

The present invention relates to methods of synthesizing DNA molecules and to reagents and kits for practicing the method.

BACKGROUND OF THE INVENTION

Conventional cloning techniques rely upon T4 DNA ligase catalyzed ligation of DNA molecules with compatible cohesive or blunt termini. Ligation of cohesive termini is enabled by the formation of Watson-Crick base pairs between nucleotides present at the termini of the two molecules to be ligated. Ligation of molecules with blunt termini is less efficient, since base-pairing does not occur between the termini, and blunt end ligations therefore require higher concentrations of DNA and ligase.

There are several problems inherent with the use of T4 DNA ligase as a catalyst for DNA ligation: 1) T4 DNA ligase cannot catalyze the ligation of DNA molecules with incompatible termini. 2) There is a high frequency of intramolecular ligation when two or more species of DNA to be ligated contain compatible cohesive termini. To reduce the background or intramolecular ligation, it is first necessary to remove the 3' phosphate from one or more of the DNA species prior to ligation. 3) It is not possible to directionally ligate two species of DNA that contain compatible termini. 4) Site-specific ligation cannot occur when three or more species of DNA with compatible termini are present in the reaction.

There is a need for improved methods of DNA ligation. Applications of such improved method include cloning and polymerase chain reaction (PCR) protocols.

PCR is a powerful tool for producing multiple copies of a DNA molecules. Using PCR, it is possible to amplify DNA sequences to create thousands and millions of identical copies of a DNA molecule. PCR is thus used to clone DNA molecules from sources having at least a single copy of the sequence to be cloned.

PCR operates by providing primers, i.e. short single stranded polynucleotides which have sequences that are complementary to sequences of a portion of the nucleic acid molecule to be amplified. When PCR is performed, the primers and the DNA molecule to be amplified are combined and the temperature raised to denature the DNA molecule to be amplified into single stranded molecules. That is the double stranded DNA molecule dissociates into a sense strand and an antisense strand. The temperature is then lowered to promote hybridization of complementary sequences. Multiple copies of two primers are usually provided, one primer hybridizes to the sense strand of the sequence to be amplified and one primer hybridizes to the antisense strand. Using a thermostable polymerase and free nucleotides, a nucleotide molecule complementary to the sense strand is assembled by adding nucleotides to the 3' end of primer that is hybridized to the sense strand. Each free nucleotide added is complementary to the nucleotide on the sequence to be amplified. As the polymerization continues, a single stranded polynucleotide molecule is assembled nucleotide by nucleotide to be complementary to the sense strand of the sequence to be amplified starting from the 3' end of the primer and proceeding in the direction 5' to 3'. Simultaneously, using polymerase and free nucleotides, a nucleotide molecule complementary to the antisense strand is assembled by adding nucleotides to the 3' end of primer that is hybridized to the antisense strand. Each free nucleotide added is complementary to the nucleotide on the sequence to be amplified. As the polymerization continues, a single stranded polynucleotide molecule is assembled nucleotide by nucleotide to be complementary to the antisense strand of the sequence to be amplified starting from the 3' end of the primer and proceeding in the direction 5' to 3'. The temperature is then raised to dissociate hybridized complementary sequences after which the temperature is again lowered to promote hybridization. The primers hybridize to the original DNA molecule as well as to the molecules synthesized in the original polymerization. Once hybridized, the polymerase assembles the primers and free nucleotides into a DNA molecule which has a full length complementary sequence to the molecule that the primer is hybridized to. After numerous rounds of lowering temperature, hybridizing primers to molecules, formation of sequences complementary to the molecules by polymerization, raising the temperature to dissociate hybridized and repeating the hybridization/polymerization cycles, most of the amplification products are molecules with sequences identical to the sequence of the original molecule between the two primers.

One shortcoming of PCR is that there is a limit to how long a sequence can be amplified using the technology. If a sequence is greater than the limit for PCR can effectively be used for amplification, it must be amplified as a series of PCR products representing adjacent portions of the final desired molecules. The series of PCR products are ligated together to form the final desired molecules.

There is a need for compositions and methods for amplifying DNA molecules that have sequences which exceed the limit beyond which PCR is effective. There is a need for compositions and improved methods for ligating adjacent PCR products. There is a need for compositions and improved methods for ligating non-adjacent PCR products into one contiguous molecule.

SUMMARY OF THE INVENTION

The present invention relates to chain reaction cloning (CRC) and to reagents and kits for performing chain reaction cloning methods.

The present invention relates to a convenient one step process that will allow site-specific ligation of DNA molecules with compatible termini in a product-driven reaction. This method utilizes the amplification capability of CRC catalyzed by thermostable DNA ligases. In addition, the method will catalyze the ligation of DNA molecules containing incompatible termini in both product and non-product driven reactions.

The present invention can be used in a number of applications such as, for example: the site specific ligation of DNA fragments generated by restriction enzyme digestion, DNAse digestion, chemical cleavage, enzymatic or chemical synthesis. An example of enzymatic synthesis would be PCR synthesis of DNA.

BRIEF DESCRIPTION OF THE FIGURES

FIGS. 10A and 10B show the strategy used to construct the chimeric kanamycin resistance gene described in Example 1. Arrows indicate PCR primers or CRC bridge oligomers, with their MPV numbers (Table 1) indicated above or below. FIG. 10A shows the PCR strategy to amplify individual fragments from the indicated templates. The promoter fragment encompasses the promoter and the 5' untranslated region of the aph(3')-Ia gene present in pUC4K, including the Shine-Dalgarno sequence. The coding region fragments are derived from the ant(4')-Ia gene in pUB110; primer MPV40 alters the Eco47III site. The terminator fragment is also derived from the aph(3')-Ia gene in pUC4K. FIG. 10B shows the CRC strategy to link the four PCR fragments as described in Example 1. After CRC was performed, some of the sample was amplified by PCR with MPV37 and MPV44.

FIG. 11 shows the sequence of the translation initiation region of the engineered ant(4')-Ia gene. The vertical line indicates the junction generated by CRC between the promoter and coding region. The Shine-Dalgarno box is underlined. Two reading frames are shown: the upper reading frame represents the desired sequence of the ant(4')-Ia gene but begins with GTG, while the lower begins with ATG but is out of frame and terminates quickly (asterisk).

FIGS. 12A and 12B show the strategy to reconstruct the ant(4')-Ia gene as described in Example 1. FIG. 12A shows the PCR amplification of fragments from pGEMkm$^{ant}$. Primer MPV62 incorporates the base changes required to alter the first two codons. FIG. 12B shows the CRC strategy to link the two PCR fragments. After CRC was performed, some of the sample was subjected to PCR with MPV64 and MPV63.

FIG. 13 shows the DNA sequence of the chimeric kanamycin resistance gene (SEQ ID NO:1) generated according to Example 1. The initiation and stop codons are underlined and positions of the MPV primers are indicated.

FIG. 15A shows schematic diagrams of two plasmids: plasmid 19 and plasmid 24. FIG. 15B shows results from Western blots of RD cells transfected with plasmid 24 (lanes 2,3), plasmid 23 (lanes 4,5) and plasmid 19 (lanes 6,7) as described in Example 1. Lane 1 contains protein molecular weight markers, from top to bottom of blot: 175, 83, 62, 47.5, 32.5, 25, 16.5 and 6.5 kd in size.

DETAILED DESCRIPTION OF THE INVENTION

Figure 1A:
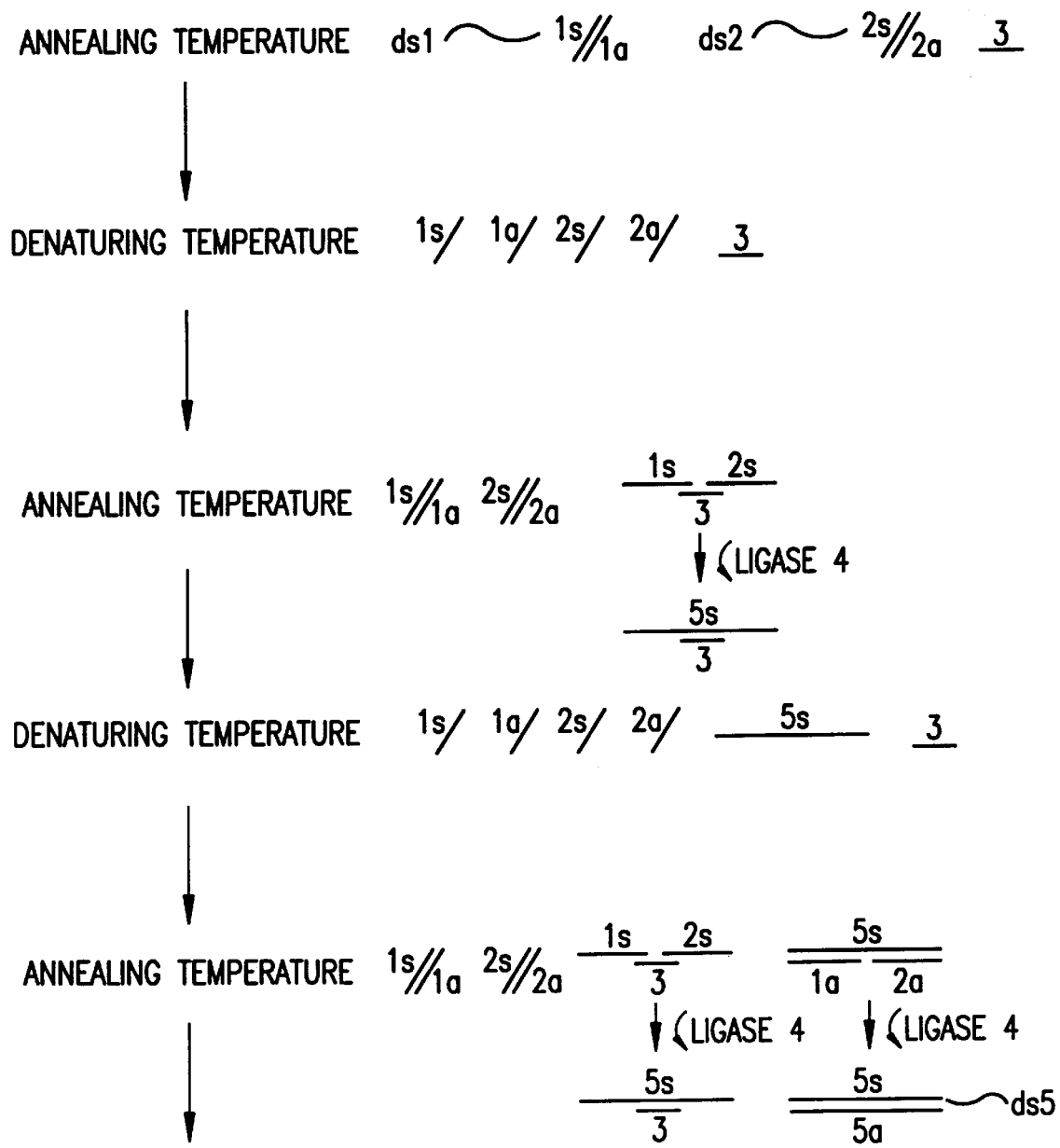
FIG. 1 shows ligation of two smaller double stranded molecules into a larger double stranded molecule according to the invention using a single bridging oligonucleotide as an initial template.

As used herein, the term "composite nucleic acid molecule" is meant to refer to a nucleic acid molecule that is synthesized by ligating at least two separate nucleic acid molecules. A composite nucleic acid molecule is also referred to herein as a "larger DNA molecule" when referring to the product of ligation of two smaller DNA molecules.

The "melting temperature" or "Tm" is calculated as follows:

$$Tm = (16.6 \times \log C) + 81.5 + (0.41 \times \% \ GC) - (675/L)$$

C = Concentration in molarity of the positive ions. (where C<0.5M)

L = Length of the oligo (where L<100)

% GC = % GC of matched (base paired) nucleotides

As used herein, the term "denaturing" is meant to refer to the dissociation of a double stranded DNA molecule into single stranded molecules including the dissociation of hybridized nucleic acid molecules of unequal length into single stranded molecules. In addition, "denaturing" means partial dissociation of double stranded DNA such that the termini of the double stranded DNA are available for hybridization to the bridging oligonucleotide. A preferred denaturing temperature is at least the Tm of the oligonucleotide set plus up to 5° C. (Tm+5° C.). For most oligonucleotide sets, the denaturing temperature range is 55–98° C.

As used herein, the term "annealing" is meant to refer to the hybridization of single stranded molecules with complementary sequences including the hybridization of nucleic acid molecules of unequal lengths. A preferred annealing temperature is the lowest Tm of the oligonucleotide set minus 0–5° C. (Tm–5° C.). For most oligonucleotide sets, the annealing temperature range is 40–70° C.

The present invention uses a thermostable ligase to ligate single stranded molecules together in a series of ligation reactions which occur in a cycle of temperature changes alternating between annealing temperatures and denaturing temperatures such that DNA molecules present in the reaction mixture alternate between existing as hybridized DNA molecules made up of single stranded molecules hybridized to each other at complementary sequences, and existing as single stranded molecules or as partial single stranded molecules. According to the present invention, nucleic acid molecules are assembled from smaller nucleic acid molecules by a series of ligation reactions. Using a thermostable ligase, nucleic acid molecules can be specifically linked to each other as single stranded molecules without the need for modifying the end of one of the two molecules being joined. The present invention uses denaturing temperature to convert double stranded nucleic acid molecules into single stranded molecules. The ends of the single stranded molecules are brought together by hybridizing to a template which is either provided as part of the reaction reagents or, after completed cycles, formed by earlier ligation reactions. The use of the template ensures that two single stranded nucleic acid molecules which are intended to be linked are aligned in proximity to each other in correct orientation to allow for the proper 3' end to be adjacent to the 5' end of the molecule to which it is to be ligated. Once oriented by the template, the ligase catalyzes the reaction which covalently joins the two nucleic acid molecules into a single, larger nucleic acid molecule that includes a sequence complementary to the template. The nucleic acid molecules are subsequently subject to denaturing conditions in which the double stranded molecule formed by the ligated nucleic acid molecules and the template cease to hybridize to each other and become single stranded molecules. The conditions are then changed to again favor hybridization of complementary nucleotide sequences. In product driven reactions, in this annealing step, the ligated molecule becomes a template for orienting unligated, single stranded nucleic acid molecules with nucleotide sequences complementary to the nucleotide sequences of the ligated molecule. Accordingly, after a series of alternating denaturing and annealing/ligation steps, nucleic acid molecules are generated from small nucleic acid molecules.

The present invention thus provides the means to generate larger nucleic acid molecules from smaller ones without the need to treat the ends in such a way to ensure specific binding of two molecules in correct orientation. Rather, the template ensures correct orientation and specific ligation. The present invention allows for the ligation of multiple components without the need for intervening steps. Using a thermocycler, a heat stable ligase and the proper starting materials, the series of reactions can proceed with out intervention.

As an initial reaction, at least one bridging oligonucleotide is provided as a template. The bridging oligonucleotide has a nucleotide sequence that includes, from its 3' to 5' ends, at least 10 and preferably 10–40 nucleotides complementary to equal number of the most 3' nucleotides of the 3' end of a first single stranded nucleic acid molecule and at least 10 and preferably 10–40 nucleotides complementary to equal number of the most 5' nucleotides of the 5' end of a second single stranded nucleic acid molecule. Thus when the first single stranded nucleic acid molecule and second single stranded nucleic acid molecule are combined together with the bridging oligonucleotide under annealing conditions, i.e. conditions under which complementary nucleotide sequences of nucleic acid molecules hybridize, the complementary sequences of the 3' end of the first single stranded molecule and the complementary sequences of the 5' end of the second single stranded nucleic acid molecules hybridize to the bridging oligonucleotide and are oriented adjacent to each other. In this orientation, the two ends are ligated by the thermostable ligase forming from the two smaller single stranded molecules a first larger single stranded molecule. The bridging oligonucleotide serves as a template to bring together the two smaller single stranded molecules in proper orientation to be ligated.

In some embodiments, a single bridging oligonucleotide is provided as a template for a single ligation reaction between single stranded nucleic acid molecules which are the sense or antisense strands of two nucleic acid molecules to be ligated. Upon restoration to the denaturing conditions, the bridging oligonucleotide is no longer hybridized to the ligated molecule. The bridging oligonucleotide serves as a template for the single ligation reaction between single stranded nucleic acid molecules which are the sense or antisense strands of two nucleic acid molecules to be ligated. The ligated molecule serves as a template for the ligation reaction between single stranded nucleic acid molecules which are the other of the sense or antisense strands of two nucleic acid molecules to be ligated. Thus, in the first round, a single ligation reaction is produced. In the second round, two reactions are produced.

In some embodiments, two bridging oligonucleotides are provided as templates for two ligation reactions, one between single stranded nucleic acid molecules that are the sense strands of two nucleic acid molecules to be joined and the other one between single stranded nucleic acid molecules that are the antisense strands of two nucleic acid molecules to be ligated. Upon restoration to the denaturing conditions, the bridging oligonucleotides are no longer hybridized to the ligated molecules. The bridging oligonucleotides serve as templates for the two ligation reactions. Similarly, the ligated molecules also serve as templates for single stranded molecules with complementary sequences. Thus, in the first round, two ligation reactions are produced with two templates. In the second round, two reactions are produced with four templates.

In some embodiments, CRC may be used to produce large circular molecules from smaller molecules. In such embodiments, a bridging oligonucleotide is provided which circularizes the molecule by ligating the 5' end to the 3' end of a single molecule.

The ability to site-specifically ligate two or more DNA molecules containing compatible or non-compatible termini simplifies DNA cloning. Clonings involving the ligation of more than two DNA molecules can be done in one step. Although ligation of more than two DNA molecules can be accomplished by T4 DNA ligase, the efficiency is poor and the screening procedure for isolating the correct ligation product is arduous.

For example, a singular fragment will be cloned into a vector in two orientations using T4 ligase. Directional ligation can be partially achieved by the use of fragments that contain two non-compatible ends. CRC ensures directionality in cloning because only those fragments that hybridize correctly to the oligo can be ligated. An example is given assuming a large number of oligos with compatible termini are involved. When ligating multiple fragments with T4 ligase, the number of ligation products are numerous, and usually greater than a unit length. A unit length is defined as a ligation product that has each fragment represented once. However, this is not generally the case. Assuming the ligation is stopped following the formation of a unit length, the number of recombinants generated is represented by the formula $2(n^n)$, in which only one is the correctly ligated molecule (In the formula, n=number of fragments). Using CRC to ligate these fragments ensures the formation of unit lengths and the number of such recombinants theoretically equal one per ligated molecule, thus increasing the chances of scoring for the correct ligation product by orders of magnitude. Screening CRC products is simplified since the correct product is always obtained as CRC precludes ligation of termini that are not brought into close proximity by a bridge oligonucleotide.

Thermostable ligase, also referred to as "DNA LIGASE heat-stable, may be obtained from Epicentre Technologies, (Madison, Wis.). The concentration of thermostable ligase in a reaction is preferably 1–50 units/100 ul reaction. In some embodiments, 5 units per 100 ul reaction is used.

The amount of bridging oligonucleotide provided in a reaction mixture ranges from 1000 fold less to 1000 fold more relative to the amount of DNA present for ligation. In some preferred embodiments, the ratio is 1 to 1.

The amount of starting material provided in the reaction mixtures ranges from 0.1 ng to 100 ug DNA.

In some embodiments, the entire CRC reaction can be done in a single cycle.

The number of cycles of alternating denaturing and annealing temperature is usually 5 to 50, preferably 30.

Figure 1B:
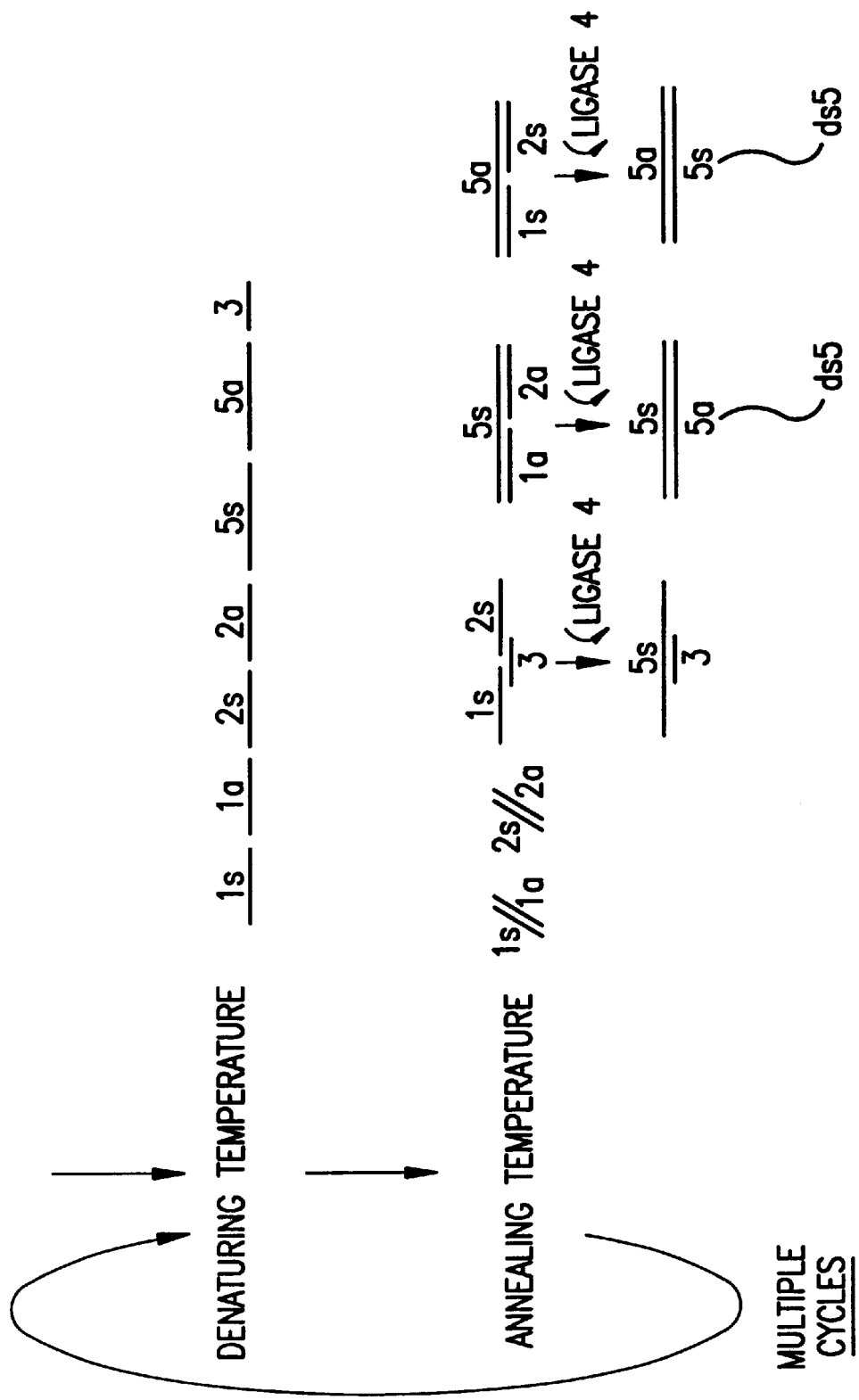

FIG. 1 shows the ligation by the methods of the invention using a single bridging oligonucleotide 3 whereby two smaller double stranded molecules ds1 and ds2 form a larger double stranded molecule ds5. The smaller double stranded molecules ds1 and ds2 are made up of single stranded molecules 1s and 1a, and 2s and 2a, respectively. The molecules exist as double stranded molecules under annealing temperatures. When the temperature is elevated to denaturing temperatures, the molecules exist as single stranded molecules 1s, 1a, 2s and 2a. In the presence of a bridging oligonucleotide 3 which has a sequence complementary to the 3' most bases of single stranded molecule is and the 5' most bases of single stranded molecule 2s and a thermostable ligase 4, the temperature is lowered to annealing temperature and molecules with complementary sequences hybridize. Some of the single stranded molecules 1s, 1a, 2s and 2a reform double stranded molecules ds1 and ds2 and additionally some copies of single stranded molecules is and 2s hybridize to bridging oligonucleotide 3. The thermostable ligase 4 ligates the 3' end of single stranded molecule 1s to the 5' end of the single stranded molecule 2s to form a larger single stranded molecule 5s which is the sense strand of the larger double stranded molecule ds5. The temperature is elevated to denaturing temperature and the molecules exist as single stranded molecules 1s, 1a, 2s, 2a, 5s and 3. The temperature is again lowered to annealing temperature and molecules with complementary sequences hybridize. Some of the single stranded molecules 1s, 1a, 2s and 2a again reform double stranded molecules ds1 and ds2 and additionally some copies of single stranded molecules is and 2s hybridize to bridging oligonucleotide 3. In addition, single stranded molecules 1a and 2a hybridize to single stranded molecule 5s. The thermostable ligase 4 ligates the 3' end of single stranded molecule 1s to the 5' end of the single stranded molecule 2s to form a larger single stranded molecule 5s which is the sense strand of the larger double stranded molecule ds5 and also ligates the 3' end of single stranded molecule 2a to the 5' end of the single stranded molecule 1a to form a larger single stranded molecule 5a which is the antisense strand of the larger double stranded molecule ds5. The temperature is again elevated to denaturing temperature and the molecules exist as single stranded molecules 1s, 1a, 2s, 2a, 5s, 5a and 3. The temperature is again lowered to annealing temperature and molecules with complementary sequences hybridize. Some of the single stranded molecules 1s, 1a, 2s and 2a again reform double stranded molecules ds1 and ds2 and some copies of single stranded molecules 5s and 5a form double stranded molecule ds5. In addition, some copies of single stranded molecules is and 2s hybridize to bridging oligonucleotide 3, some copies of single stranded molecules 1a and 2a hybridize to single stranded molecule 5s and some copies of single stranded molecules is and 2s hybridize to single stranded molecule 5a. The thermostable ligase 4 ligates the 3' end of single stranded molecule 1s to the 5' end of the single stranded molecule 2s to form a larger single stranded molecule 5s which is the sense strand of the larger double stranded molecule ds5 and also ligates the 3' end of single stranded molecule 2a to the 5' end of the single stranded molecule 1a to form a larger single stranded molecule 5a which is the antisense strand of the larger double stranded molecule ds5. The temperature is again elevated to denaturing temperature and the molecules exist as single stranded molecules 1s, 1a, 2s, 2a, 5s, 5a and 3. By alternatingly cycling of temperature between annealing temperature and denaturing temperature, the larger single stranded molecules 5s and 5a serve as templates for bringing together single stranded molecules 1a and 2a, and 1s and 2s, respectively, in proper orientation, alignment and proximity to be ligated by the thermostable ligase.

Figure 2:
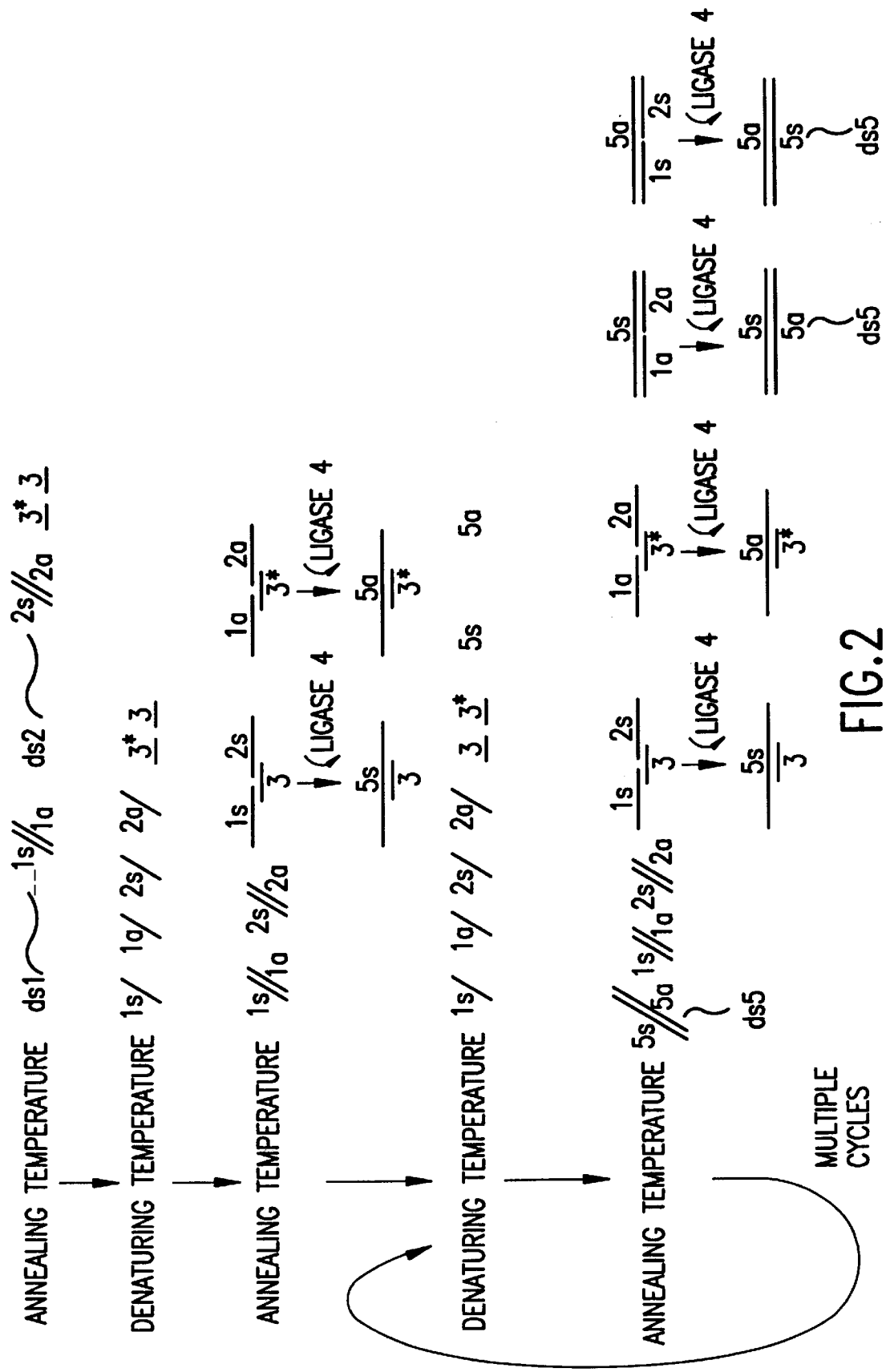
FIG. 2 shows ligation of two smaller double stranded molecules into a larger double stranded molecule according to the invention using two bridging oligonucleotides as initial templates.

FIG. 2 shows a similar reaction to that shown in FIG. 1 but using two bridging oligonucleotides instead of one. By using the second bridging oligonucleotide 3* which has a sequence complementary to a portion of the sequence of single stranded molecules 1a and 2a, the larger single stranded molecule 5a is formed at an earlier cycle. The formation of the larger double stranded molecule ds5 is not changed.

Multiple ligations may be performed simultaneously. It is contemplated and intended that two, three, four, five etc. smaller molecules may be ligated together in order to form a single larger molecule. Those having ordinary skill in the art can readily adapt the description for ligating two smaller molecules to a single larger molecule to design protocols whereby multiple smaller molecules are joined.

In one preferred embodiment, the present invention is used in conjunction with multiple simultaneous PCR reactions or that produce multiple PCR products which are then ligated together to form a larger molecule. This embodiment of invention may be described in general terms using the accompanying figures.

Figure 3:
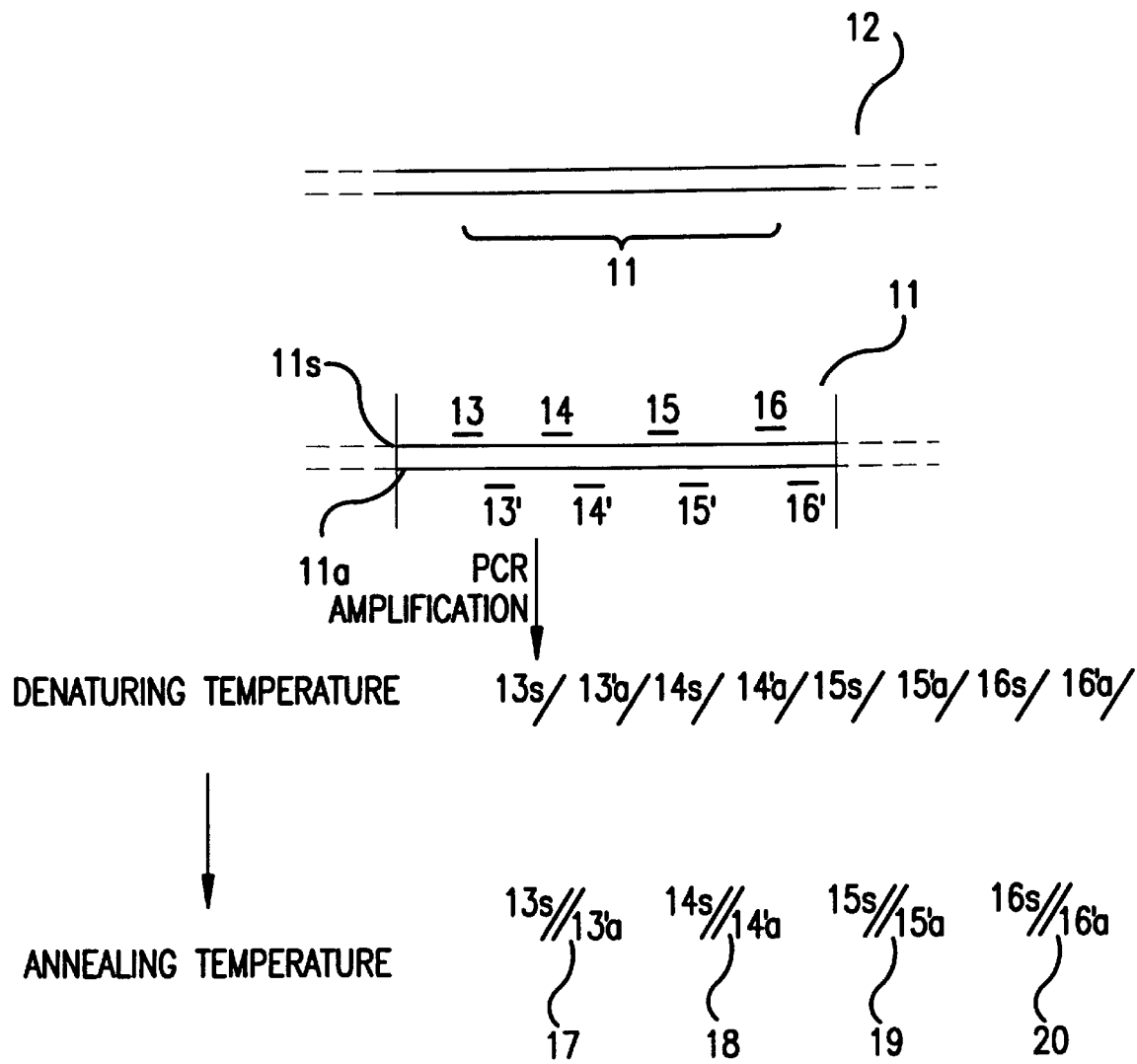
FIG. 3 is a diagram of PCR amplification of a sequences of a DNA molecule to produce PCR amplification products.

FIG. 3 shows a PCR reaction which generates multiple PCR amplification products which are ligated together using the present invention in order to form a composite nucleic acid molecule that includes the entire sequence spanning the most 5' and the most 3' primers used. According to FIG. 3, a sequence 11 of a nucleic acid molecule 12 is amplified by PCR using four sets of primers 13 and 13', 14 and 14', 15 and 15', 16 and 16'. The sequence 11 consists of a sense strand 11s and an antisense strand 11a. Primers 13, 14, 15 and 16 each hybridize to a sequence on the sense strand 11s of the sequence 11. Primers 13', 14', 15' and 16' each hybridize to a sequence on the antisense strand 11a of the sequence 11. When PCR is performed on the nucleic acid molecule 12 using the four sets of primers 13 and 13', 14 and 14', 15 and 15', 16 and 16', eight single stranded molecules are formed 13s, 13'a, 14s, 14'a, 15s, 15'a, 16s, 16'a which when complementary strands are annealed form four amplification products 17, 18, 19, 20.

Figure 4A:
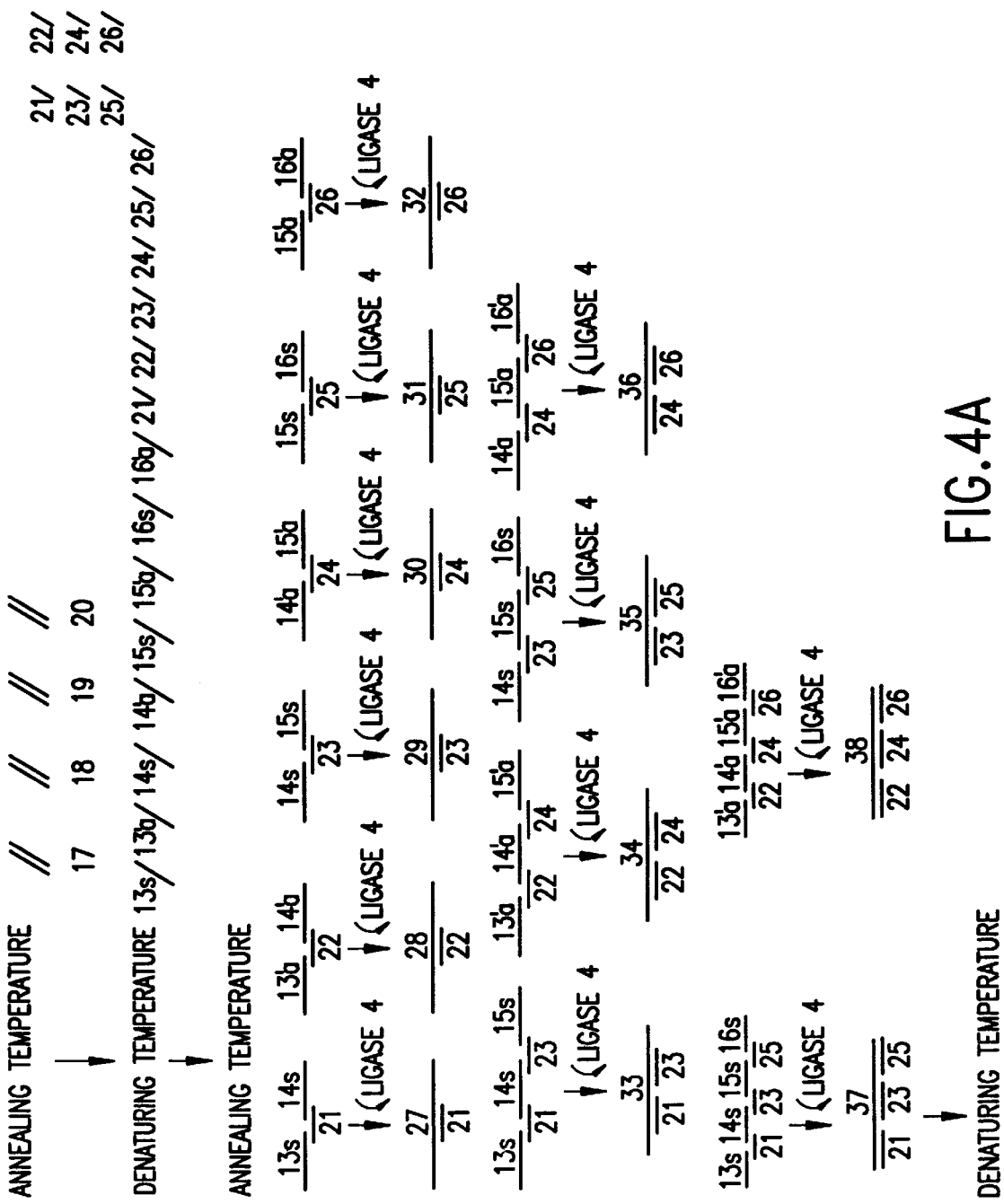
FIG. 4 is a diagram of the chain reaction cloning technique of the present invention using the PCR amplification products.

FIG. 4 shows the ligation of the four amplification products 17, 18, 19, 20 to produce a DNA molecule with a sequence identical to sequence 11 of nucleic acid molecule 12. The temperature of the four amplification products 17, 18, 19, 20 is elevated to promote dissociation of the double stranded molecules, producing eight single stranded molecules 13s, 13'a, 14s, 14'a, 15s, 15'a, 16s, 16'a. Six bridging oligonucleotides 21, 22, 23, 24, 25, 26 are used as templates. Bridging oligonucleotide 21 has a sequence which is complementary to the 3' end of the single stranded molecule 13s and the 5' end of the single stranded molecule 14s. Bridging oligonucleotide 22 has a sequence which is complementary to the 5' end of the single stranded molecule 13a and the 3' end of the single stranded molecule 14a. Bridging oligonucleotide 23 has a sequence which is complementary to the 3' end of the single stranded molecule 14s and the 5' end of the single stranded molecule 15s. Bridging oligonucleotide 24 has a sequence which is complementary to the 5' end of the single stranded molecule 14a and the 3' end of the single stranded molecule 15a. Bridging oligonucleotide 25 has a sequence which is complementary to the 3' end of the single stranded molecule 15s and the 5' end of the single stranded molecule 16s. Bridging oligonucleotide 26 has a sequence which is complementary to the 5' end of the single stranded molecule 15a and the 3' end of the single stranded molecule 16a.

The eight single stranded molecules 13s, 13'a, 14s, 14'a, 15s, 15'a, 16s, 16'a are combined with the six bridging oligonucleotides 21, 22, 23, 24, 25, 26 and the temperature is lowered to promote annealing of complementary nucleotide sequences. Under such conditions, single stranded molecules can hybridize to bridging oligonucleotides. Single stranded molecules 13s and 14s can hybridize to bridging oligonucleotide 21 to form complex 27. Single stranded molecules 13'a and 14'a can hybridize to bridging oligonucleotide 22 to form complex 28. Single stranded molecules 14s and 15s can hybridize to bridging oligonucleotide 23 to form complex 29. Single stranded molecules 14'a and 15'a can hybridize to bridging oligonucleotide 24 to form complex 30. Single stranded molecules 15s and 16s can hybridize to bridging oligonucleotide 25 to form complex 31. Single stranded molecules 15'a and 16'a can hybridize to bridging oligonucleotide 26 to form complex 32. It is possible that complexes can include more than two single stranded molecules and more than one bridging oligonucleotides such as complexes formed by single stranded molecules 13s, 14s and 15s can hybridize to bridging oligonucleotides 21 and 23 to form complex 33. Single stranded molecules 13'a, 14'a and 15'a can hybridize to bridging oligonucleotides 22 and 24 to form complex 34. Single stranded molecules 14s, 15s and 16s can hybridize to bridging oligonucleotides 23 and 25 to form complex 35. Single stranded molecules 14'a, 15'a and 16'a can hybridize to bridging oligonucleotides 24 and 26 to form complex 36. Complexes may form from four sense or four antisense single stranded molecules. For example, complexes may formed by single stranded molecules 13s, 14s, 15s and 16s hybridizing to bridging oligonucleotides 21, 23 and 25 to form complex 37. Similarly, single stranded molecules 13'a, 14'a, 15'a and 16'a can hybridize to bridging oligonucleotides 22, 24 and 26 to form complex 38. Once the complexes are formed, the thermostable ligase 4 ligates adjacent nucleotides of single stranded molecules. Upon raising the temperature to a level sufficient for dissociation of double stranded DNA, the bridging oligonucleotide dissociates from the ligated single stranded molecules. Lowering the temperature to annealing temperature brings about the same complex formation as described in the annealing step above and additionally complexes formed using newly formed single stranded molecules 27–38 as templates for joining two, three and four smaller single stranded molecules into one larger single stranded molecules. After multiple denaturing/annealing cycles multiple copies of both the sense and antisense strands of 11 are formed which under annealing conditions provides multiple copies of a double stranded molecule consisting of 11 formed from PCR amplification products 17, 18, 19 and 20. In some embodiments, both sense and antisense primers are used. In some embodiments, only sense primers are used. In some embodiments, only antisense primers are used.

Thus, the present invention may be used to form single double stranded molecules from multiple adjacent PCR products thereby effectively allowing for the PCR amplification of very large nucleotide sequences through the amplification of adjacent sequences and ligation of such products. Alternatively, the present invention may be used to form single double stranded molecules from multiple non-adjacent PCR products thereby effectively allowing for the PCR amplification of very large nucleotide sequences through the amplification of adjacent sequences and ligation of such non-adjacent sequences in a single product.

In FIGS. 5A, 5B, 6 and 8 only relevant annealings are shown. That is, for the purpose of brevity, only annealings that result in new product formation are shown. For example, in FIG. 5A, in cycle 1, n>3, A can reanneal to A' and B can reanneal to B' and no new product is generated. These annealings are not favored at any point in the reaction as there is a molar excess of o' with respect to A and B. Therefore most of A and B will anneal to o'. In addition, some subset of o' will hybridize only to A or B. In cycle 2 N>3, AB can anneal to o' and no new product is generated. In cycle 3, n>3, AB and A'B' can reanneal to each other and no new product is generated.

Figure 5A:
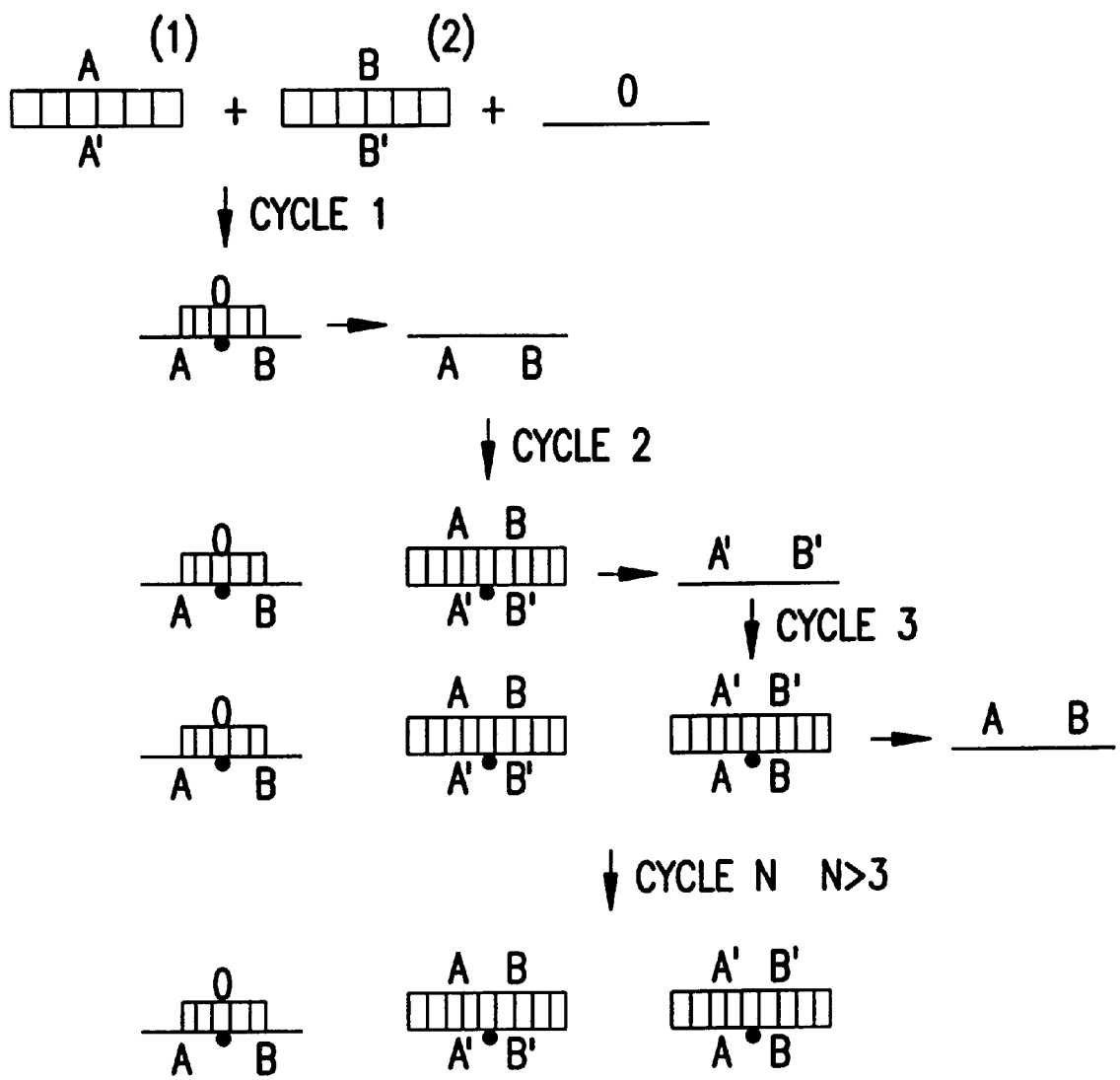
FIGS. 5A and 5B depict examples of product driven reactions.
Figure 5B:
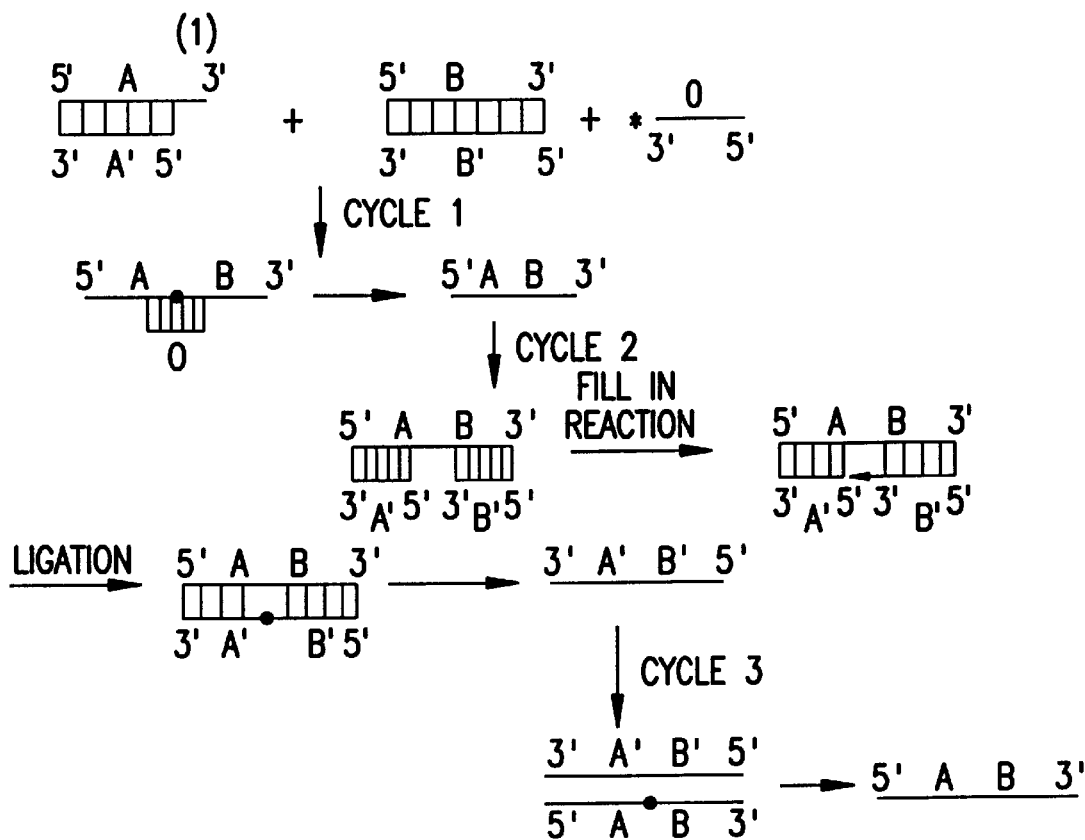

FIG. 5A and 5B are examples of product driven reactions. FIG. 5A depicts DNA fragments containing compatible termini and their participation in a product driven reaction. The picture example is of two blunt ended DNA molecules. Other types of termini that can be ligated to each other in a product-driven reaction are a 3' overhang to a blunt terminus and a 5' overhang to a blunt terminus and also a 5' overhang and a 3' overhang when a heat stable non-strand displacement DNA polymerase (such as: Amplitherm DNA polymerase, Epicentre Technologies Madison Wis.; Tfl DNA polymerase, Epicentre Technologies Madison Wis., Promega Madison Wis.; Tth DNA polymerase, Epicentre Technologies Madison Wis., Promega Madison Wis.; Replitherm DNA polymerase, Epicentre Technologies Madison Wis.; Pfu DNA polymerase, Stragene LaJolla Calif.; and Exo-Pfu DNA polymerase, Stragene LaJolla Calif.) is included together with heat stable DNA ligase (Ampligase, Epicentre Technologies, Madison Wis.)in the reaction as shown in FIG. 5B. Molecules containing 5' overhangs only or 3' overhangs only must first be blunt ended prior to ligation. Ligation of blunt ended molecules occurs in a product driven reaction.

In FIG. 5A, the top strand (A) and the bottom strand (A') of DNA molecule 1, the top strand (B) and the bottom strand (B') of DNA molecule 2 are depicted. The bridge oligonucleotide is designated 0. Base pairing is indicated with vertical lines. During cycle 1, 0, which is complementary to the terminal sequences of A and B, anneals to strands A and B. Ligation of strands A and B occur, resulting in the formation of product molecule AB. Ligation is represented by the filled circle (●). In cycle 2, product AB anneals to strands A' and B', ligation of A' and B' occur, and product A'B' is formed. In cycle 3, A'B' acts as a catalyst for the formation of product AB. In cycle n>3, molecules A'B' and 0 act as a catalysts for the formation of product AB while product AB acts as a catalyst for the formation of product A'B'.

In FIG. 5B, the top strand (A) and the bottom strand (A') of DNA molecule 1, the top strand (B) and the bottom strand (B') of DNA molecule 2 are depicted. DNA molecule 1 contains a 5' recessed end while DNA molecule 2 contains blunt ends. The bridge oligonucleotide is designated 0. The 3' end of of 0 contains a blocking group (*) so that 0 cannot be chain extended. Base pairing is indicated with vertical lines. During cycle 1 and cycles n>1, 0, which is complementary to the 3' terminus of A and the 5' terminus of B, anneals to strands A and B. Ligation of strands A and B occur, resulting in the formation of product molecule 5'-AB-3'. Ligation is represented by the filled circle (●). In cycle 2 and cycles n>2, product 5'-AB-3' anneals to strands A' and B'. In the presence of a non-strand displacing heat stable DNA polymerase, B' is extended until the growing B' chain incorporates the nucleotide immediately 3' of the most 5' nucleotide of A' (that is to say that the template molecule is copied up to the nucleotide located immediately 3' of the first nucleotide that is based paired with the 5' most nucleotide of A'). Ligation of A' and B' occurs, and product 5'-A'B'-3' is formed. In cycle 3 and in cycles n>3, 5'-A'B'-3' acts as a catalyst for the formation of product 5'-AB-3'.

Figure 6:
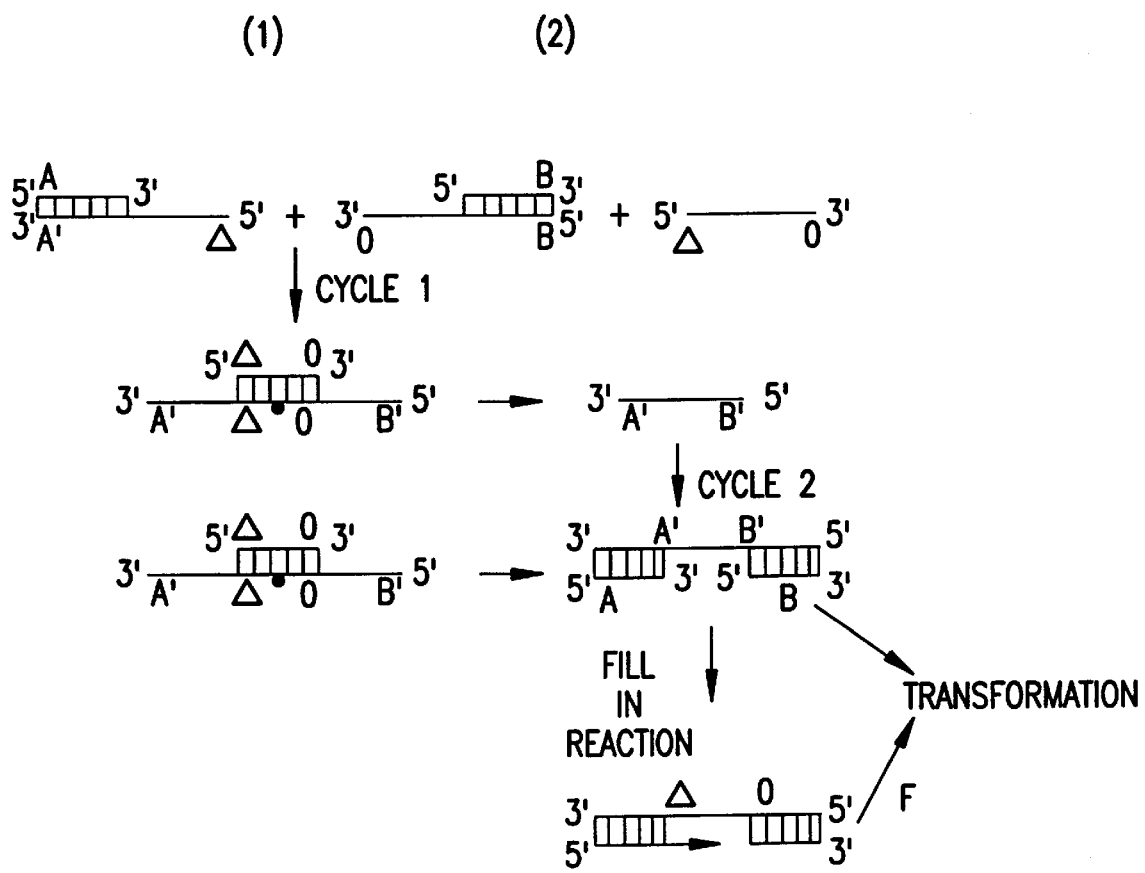
FIG. 6 is an example of a non-product driven reaction.

FIG. 6 shows an example of a non-product driven reaction (i.e. ligation of non-compatible molecules bearing a 5' overhang and a 3' overhang. An example of this would be ligation of a molecule cut with BamH1 to a molecule cut with Pst1.) In this type of reaction, the product DNA strand does not catalyze the ligation of the other DNA molecules. The picture examples depict the ligation of a DNA molecule with a 5' overhang to a DNA molecule with a 3' overhang. The ligation occurs in a non-product driven reaction in the absence of a heat stable non-strand displacing DNA polymerase. In FIG. 6, DNA molecule 1 containing the 5' overhang and DNA molecule 2 containing the 3' overhang are depicted. The Δ and ○ regions of DNA molecules 1 and 2 designate complementary sequences to the corresponding Δ and ○ regions of bridge oligonucleotide 0. During cycle 1, 0 anneals to strands A' and B'. Ligation of strands A' and B' occur, resulting in the formation of product molecule A'B'. In cycle 2, product A'B'anneals to strands A and B. The gap in the molecules can be filled with a DNA polymerase and subsequently used to transform bacteria or used to transform bacteria with no prior fill in. In a non-product driven reaction, CRC may be practiced by holding the reaction at one temperature for a long period of time, following an initial 98° C. denaturation. The temperature for holding the reaction will be the optimum for enzyme activity, ~65° C. degrees. The bridge oligos would be designed such that the Tms<65° C., preferably 55–60° C. At this temperature, the oligos will hybridize to target sequences and bring the 2 strands together, but inefficiently since the temperature is above the Tm. Following ligation, the oligo dissociates and is available for another reaction. The total separation of template DNA need not be complete, however the ends of the template DNA need to denature so as to allow the hybridization of the bridge oligo. At the end of the reaction, the reaction is heated to 98° C. and slowly cooled to allow annealing of the DNA strands.

Figure 7A:
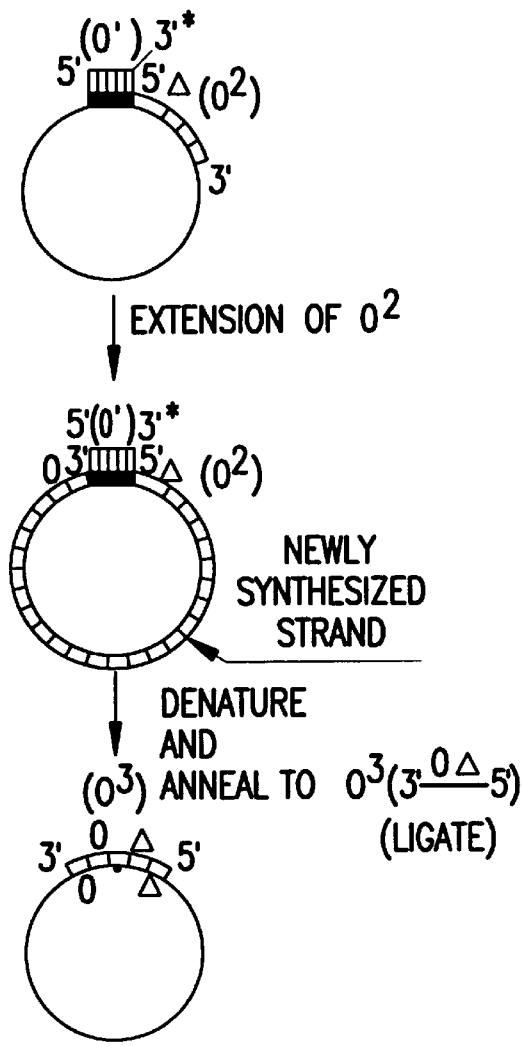
FIGS. 7A, 7B and 7C show site directed mutagenesis using methods of the present invention.
Figure 7B:
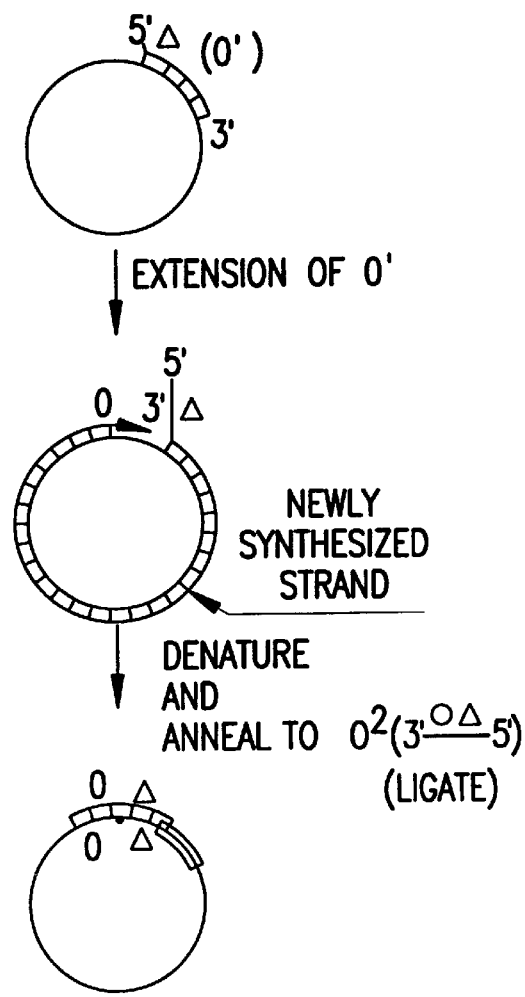
Figure 7C:
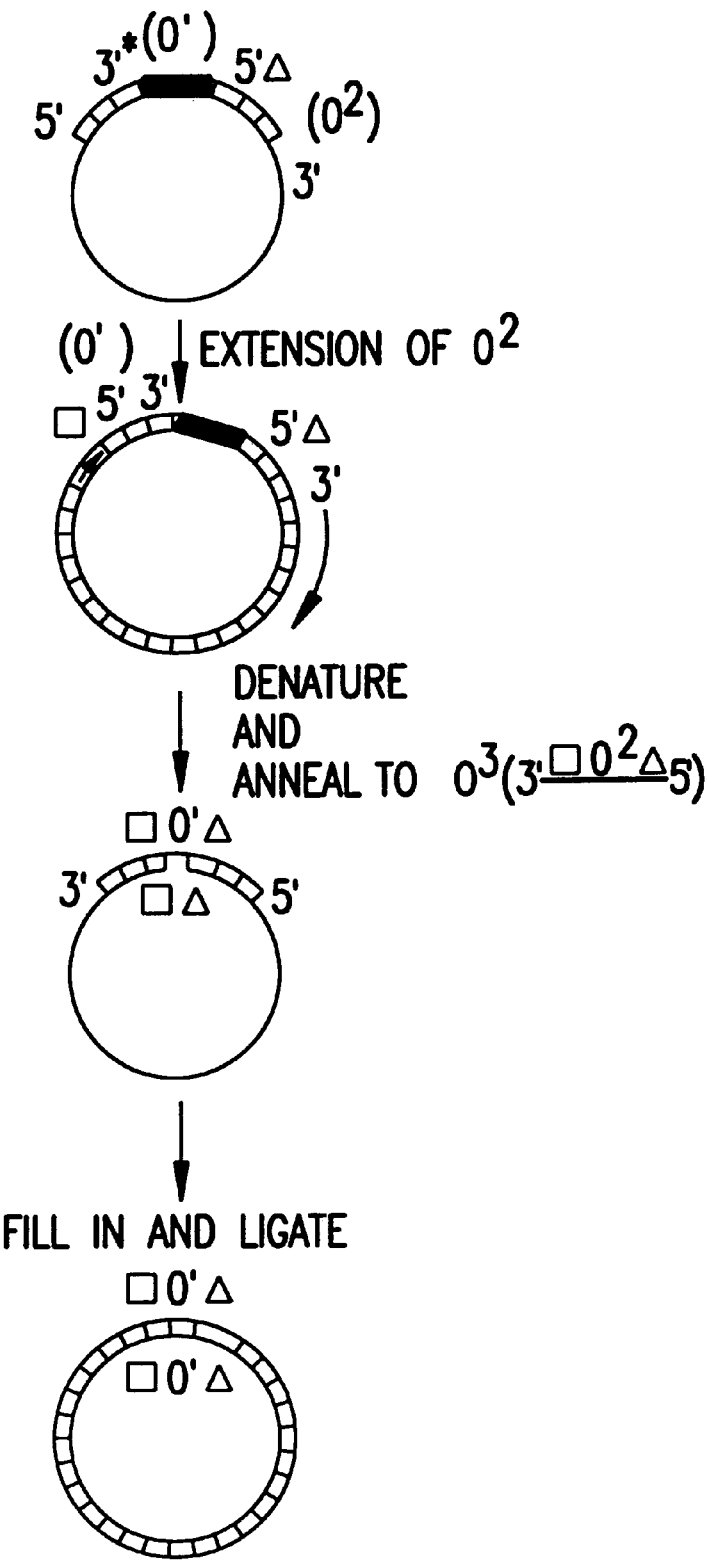

FIGS. 7A, 7B and 7C show site directed mutagenesis using methods of the present invention. In FIG. 7A, ○' is complimentary to the entire region to be deleted. As this region becomes larger, the length of ○' also becomes larger and more expensive. If the cost of ○' becomes prohibitive, the experimenter may opt to perform the experiment according to an alternative method detailed in FIG. 7C. The source of ss DNA for site-directed mutagenesis can be ss phage DNA or denatured plasmid DNA.

FIG. 7A depicts site directed deletion of sequences. The parental DNA is depicted as a single stranded circular DNA. The sequence to be deleted from the parental DNA, represented by the filled rectangle (■), is annealed to a complementary oligonucleotide, (○'), containing a 3' blocking group. The 3' block, indicated by an asterisk (*), prevents oligonucleotide extension by polymerases. Oligonucleotide 2 ($o^2$) is complementary to nucleotide located immediately 3' of the sequence to be deleted. $o^2$ is extended in the presence of a non-strand displacing DNA polymerase such as T4 DNA polymerase and dNTPs. The ends of the newly synthesized strands (represented by ○ and Δ) are annealed to the bridge oligonucleotide $o^3$ and ligated, resulting in the deleted product DNA molecule.

FIG. 7B depicts site directed insertion of sequences. The parental DNA is depicted as a single stranded circular DNA. The sequence to be inserted is shown as the non-annealed portion of ○'. The 5' terminus of ○' is represented with a Δ. Immediately flanking the 3' end of the sequence to be inserted is a sequence that is complementary to the parental DNA> ○' is extended in the presence of T4 DNA polymerase and dNTPs. The ends of the newly synthesized strands (represented by ○ and Δ) are annealed to the bridge oligonucleotide $o^2$, and ligated, resulting in the DNA produced containing an insertion (□).

In FIG. 7C, the parental DNA is depicted as a single stranded circular DNA. The sequence to be deleted from the parental DNA is represented by the filled rectangle (■). ○', complementary to the region immediately upstream of the region to be deleted, carries a 3' blocking group indicated by an asterisk (*). The 3' block prevents oligonucleotide extension. $o^2$ is complementary to nucleotide located immediately downstream of the sequence to be deleted and is extended in the presence of a non-strand displacing DNA polymerase such as T4 DNA polymerase and dNTPs. The ends of the newly synthesized strands (represented by □ and Δ) are annealed to the bridge oligonucleotide $o^3$. The bridging oligonucleotide is comprised of the sequence that is complementary to the entire ○' and is flanked on the 3' side by the complement to the □ sequence and on the 5' side to the Δ sequence. Following the fill in reaction, both strands contain the ○' sequence and have sustained the desired deletion.

Figure 8:
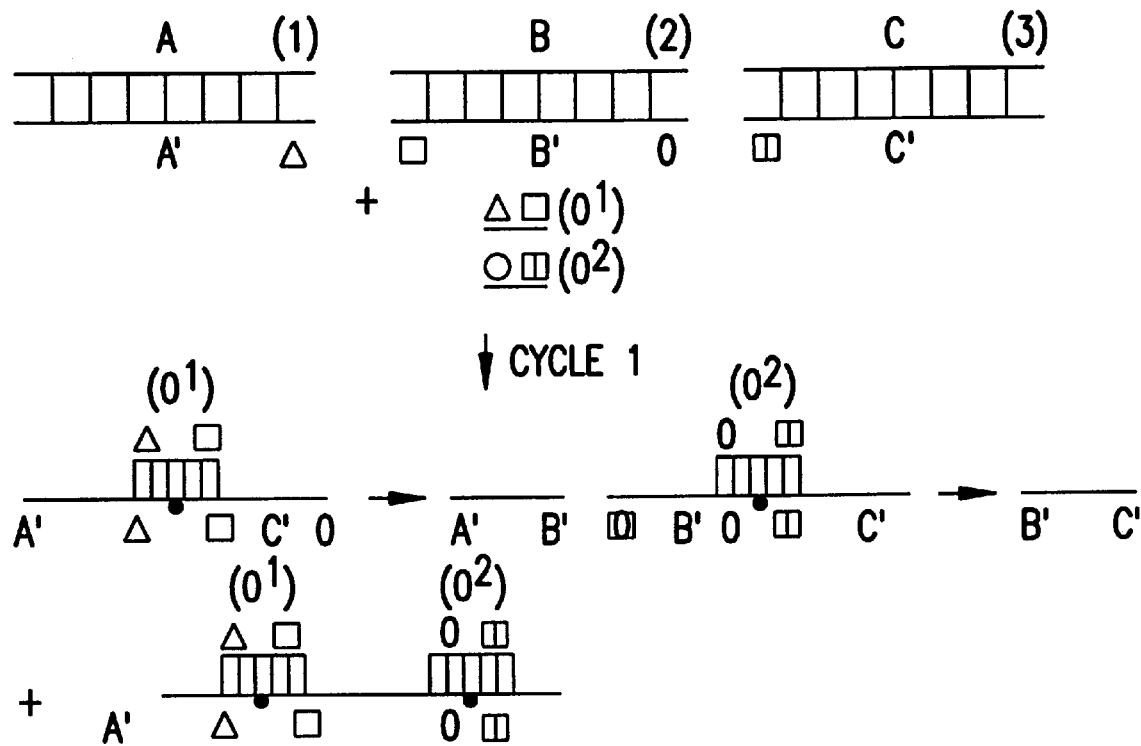
FIG. 8 shows ordered ligation using methods of the present invention.

An ordered ligation is depicted in FIG. 8. DNA molecules 1, 2 and 3 are shown. All termini of these molecules are compatible. In order to specifically ligate the Δ terminus to the □ terminus and the ○ terminus to the □□ termini, the mixture of DNA molecules is annealed to the two bridging oligonucleotides, ○' and $o^2$. Product molecules A'B', B'C' and A'B'C' are generated which in subsequent cycles act to catalyze the formation of products AB BC and ABC.

Figure 9A:
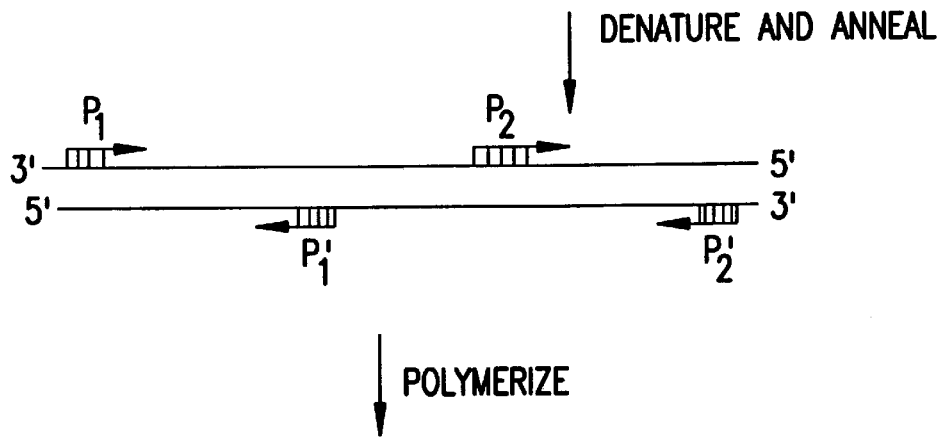
FIGS. 9A, 9B and 9C show a long range PCR ligation using a non-strand displacing heat stable DNA polymerase and heat stable ligase.
Figure 9B:
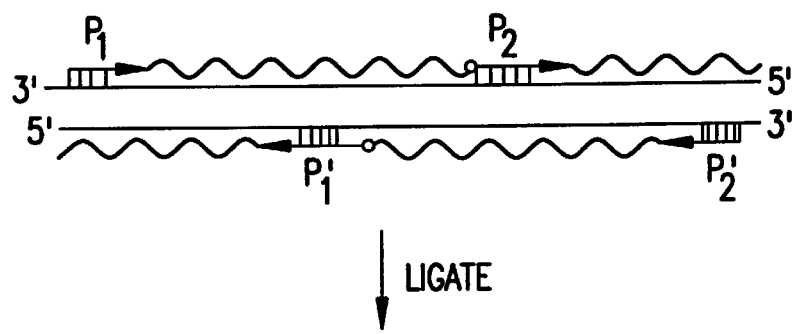
Figure 9C:
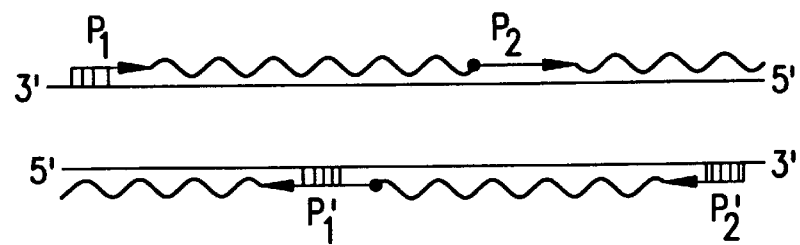

FIGS. 9A, 9B and 9C show a PCR ligation. In FIG. 9A, PCR primers p1, p2, p1' and p2' are shown annealed to the DNA templates. The primers are depicted by short lines while the single stranded DNA templates are depicted by the longer lines. FIG. 9B shows a PCR reaction that contains both a non-strand displacing heat stable DNA polymerase and a heat stable ligase, the PCR primers are chain extended. The direction of the extension is indicated by arrows. As shown in FIG. 9C, when the extending 3' terminus of the primer extension products p1 extend and p1' extend, abut the 5' terminus of the downstream primer extension products, p2 extend and p2' extend, ligation occurs resulting in covalent attachment of adjacent DNA molecules. Ligation is indicated by the filled in circle (●). PCR ligation is especially useful to make large PCR products with extension times that are short and reasonable and do not compromise enzymatic activity during the course of PCR. The extension times required in a PCR ligation method is determined by the distances between the primers p1 and p2.

CRC can also be used to enable long-range PCR. This can be accomplished by the site-specific ligation of PCR products or by performing PCR in the presence of a non-strand displacing heat stable DNA polymerase and a heat stable ligase as shown in FIGS. 9A, 9B and 9C.

CRC can also be used to specifically clone a specific fragment of DNA from a pool of DNA fragments; for example, cloning a specific DNA fragment following a limited DNAse digestion of a DNA molecule as would be done for the creation of a set of nested deletions. Another example is cloning a specific fragment of DNA following restriction enzyme digestion that yields multiple fragments of DNA. In addition, CRC can be used for site directed mutagenesis as shown above. CRC can also be used to circularize a linear piece of DNA by using a bridge oligonucleotide containing complementarity to both termini of the linear DNA.

The present invention provides kits for cloning genes into vectors. According to some embodiments, kits comprise a container having in it a vector such as plasmid, phage, viral vector, yeast artificial chromosome, or other vector into which a desired DNA molecule is to be inserted. In addition, the kits comprise adaptors which are ligated to the ends of a desired DNA molecule when combined with the desired DNA molecule in the presence of ligase. Further the kits comprise bridge oligonucleotides which will hybridize to the ends of the adaptors and the ends of the vector at the insertion point. Additionally, the kits comprise a container having heat stable DNA ligase. Optionally, the kits include DNA ligase for joining the adaptors to the desired DNA molecule.

The present invention provides improved PCR kits which, in addition to including heat stable polymerase, primers dNTPs, and vectors, further comprise bridge oligonucleotides designed to hybridize to primer sequences and vector sequences and heat stable DNA ligase. Using such kits, cDNA libraries may be prepared by PCR. The cDNA clones are inserted into vectors in the correct orientation using bridge oligonucleotides according to the invention.

EXAMPLE

INTRODUCTION

Clinical vectors have been modified to replace the aph (3')-Ia gene with a chimeric kanamycin resistance gene. To compare the ability of either backbone to express eukaryotic genes, the envelope glycoprotein D gene (HSVgD2) from herpes simplex virus 2 (HSV-2) was cloned into clinical vectors which had either one of the two kanamycin resistance genes. In tissue culture experiments, both vectors support expression of $HSVgD_2$ protein as detected by Western blot. Fermentation parameters of *E. coli* containing either vector were also compared. Growth of cells harboring the chimeric ant(4')-Ia gene was considerably enhanced when compared to cells harboring the aph(3')-Ia gene, although DNA yields per gram of cell were similar for either vector. The growth differences are most likely a consequence of the different biochemical requirements and activities of ANT(4')-IA enzyme and APH(3')-IA enzyme.

MATERIALS AND METHODS

Plasmids:

The kanamycin resistance gene aminoglycoside 3'-phosphotransferase type Ia (aph(3')-Ia) was obtained from the plasmid pUC4K (Pharmacia, Piscataway, N.J.). This *E. coli* gene for resistance to kanamycin was originally derived from Tn903.

The kanamycin resistance gene adenylyl 4'-nucleotidyltransferase type Ia (ant(4')-Ia) (Matsumura et al., *J. Bacteriology* 1984, 160:413–420 which is incorporated herein by reference) was obtained from the plasmid pUB110 (Sigma, St. Louis, Mo.). The pUB110 plasmid was originally discovered in gram positive *S. aureus.*

The clinical DNA vector is a plasmid backbone that contains a bacterial origin of replication, a composite promoter comprised of the Rous sarcoma virus (RSV) enhancer and the human cytomegalovirus (HCMV) immediate early promoter, a polylinker for insertion of a gene encoding a desired protein or antigen, an SV40 polyadenylation signal, and a kanamycin resistance gene. The original plasmid, plasmid 4, contains each of the elements described above and the kanamycin resistance aph(3')-Ia gene.

Plasmid 19 is the plasmid 4 vector with the HSV gene $HSVgD_2$ cloned between the promoter and polyadenylation signal.

Plasmid 23 is a modification of plasmid 4 in which the aph(3')-Ia gene is replaced with the chimeric ant(4')-Ia gene of the invention.

Plasmid 24 is plasmid 23 with the $HSVgD_2$ gene cloned between the promoter and polyadenylation signal.

Bacterial Strains:

*E. coli* DH10B ($F^-$ mcrA, Δ(mrr-hsdRMS-mcrBC) φ80dlacZΔM15 ΔlacX74 deoR recA1 endA1 araD139 Δ(ara, leu) 7697 galU galK λ-rpsL nupG) competent cells (Gibco-BRL, Grand Island, N.Y.) were transformed according to the manufacturer's instructions with plasmid 4, plasmid 19, plasmid 23 and plasmid 24, and grown on LB plates containing 40 μg/ml kanamycin. Plasmid DNA was purified by the alkaline lysis procedure (Sambrook, S., et al., *Molecular Cloning: A Laboratory Manual* 1989, which is incorporated herein by reference). DH10B cells were transformed with $pBLUEkm^{ant}$ and pUC4K, in order to analyze the range of activity of ant(4')-Ia and aph(3')-Ia genes, respectively, against various aminoglycosides. These experiments were carried out by Microbiology Reference Laboratory, Cypress, Calif.

Primers and Bridge Oligomers:

DNA oligomers were designed for use in polymerase chain reaction (PCR) or in chain reaction cloning (CRC as described below), and were supplied by Research Genetics, Huntsville, Ala. Table 1 lists the primers and oligomers, and FIG. 10A, 10B, 12A, 12B and 13 indicate their positions in relation to the templates and the final chimeric ant(4')-Ia sequence. PCR primers were stored as 100 μM stocks in sterile water, while bridge oligomers were stored at 1 mg/ml in sterile water.

PCR Reaction Conditions:

Reactions were performed in 50 μl volumes containing 1× PCR buffer (50 mM KCl, 10 mM Tris, pH 8.3, 1.5 mM $MgCl_2$, 0.0010 gelatin), 200 μM each dNTP, 0.2 μM each primer, 1 unit AmpliTaq® thermostable polymerase (Perkin-Elmer), and 5 ng of template DNA. Samples went through 30 cycles of 94° C. 1 minute, 72° C. 1–2 minutes in a Perkin Elmer 9600 machine.

During the first round of cloning, the engineered ant(4')-Ia gene was initially amplified to include FseI and SwaI sites at the 5' and 3' ends (primers MPV37 and MPV44), for use in future cloning experiments. When the gene was subjected to PCR to alter the first and second codons, XbaI and BamHI sites were additionally engineered onto the 5' and 3' ends of the gene (primers MPV64 and MPV63, respectively), to enable easy cloning into those same sites in pBluescript.

CRC Reaction Conditions:

Chain reaction cloning (CRC) employs a thermostable ligase to join DNA fragments in a desired order. It is often difficult to make gene constructs because DNA fragments lack either compatible restriction enzyme sites, or enzyme sites at the "right" places. This method obviates the need for such sites, because it joins fragments in a precise order determined by the experimenter. One need only know the sequence at the ends of the fragments to be joined. A "bridge" oligomer is designed which is identical to a desired junction region, and which overlaps the two fragments to be joined by approximately 20 to 25 bases on each side of the junction. The two fragments are incubated in equimolar ratios with an excess of the bridge oligo, and heated to 94° C. to melt the DNA strands. The sample is cooled to 68–72° C., enabling the bridge oligo to hybridize to the single strands from the two fragments. The oligo brings together these single strands so that the ligase can join them together. This cycle is repeated many times, and in subsequent cycles both the bridge oligo and previously joined single strands act as templates for hybridization and ligation. Once CRC is completed, a portion of the sample is usually subjected to PCR, using primers derived from the ends of the joined fragments, and the amplified DNA can be cloned and analyzed.

CRC was employed to join four fragments in a specific order to generate the engineered ant(4')-Ia gene, while two fragments were joined by CRC to generate plasmid 23.

DNA fragments used in CRC were obtained through PCR or restriction digestion. In either case, the fragments were separated on low-melt agarose gels and purified (Sambrook et al., 1989 Supra). Reactions were in 100 µl volumes containing equimolar amounts of the fragments to be ligated (up to 1 µg of each fragment), 8–10 picomoles of each bridge oligo, 1× CRC buffer (20 mM Tris, pH 8.3, 25 mM KCl, 10 mM $MgCl_2$, 0.5 mM NAD, 1% Triton X-100), and 50–100 units of Ampligase® (Epicentre, Madison, Wis.). Samples went through 50 cycles of 94° C. 1 minute, 68–72° C. 2 minutes. When CRC products were to be resolved and amplified by PCR, approximately 5% to 40% of the CRC reaction was used as template for PCR.

Subcloning, Ligations and Transformations:

Some DNA fragments obtained by PCR amplification were ligated into the plasmid pCR™3, and the ligation products were used to transform E. coli one shot™ TOP10F' cells, according to the manufacturer's instructions (Invitrogen, San Diego, Calif.). The ant(4')-Ia engineered gene was initially cloned this way, to yield plasmid pkm23. The ant(4')-Ia gene was excised from pkm23 with XbaI and BamHI and subcloned into the same sites in pGEM11Zf+ for functional testing, to yield plasmid pGEMkm$^{ant}$. DNA from pGEMkm$^{ant}$ was the template for the reconstruction of ant(4')-Ia. After the altered gene was generated by PCR and CRC, it was cleaved at engineered XbaI and BamHI ends and subcloned into those sites in pBluescript, yielding pBLUEkm$^{ant}$.

The $HSVgD_2$ gene in plasmid 19 was excised from that plasmid with KpnI and MluI. The fragment was ligated into the same sites present in plasmid 23, to yield plasmid 24.

The above conventional ligations were performed in a final volume of 10 to 15 µl, where the vector to insert molar ratio was approximately 1:3. Vectors were digested with appropriate restriction enzymes, then treated with calf intestinal alkaline phosphatase, as directed by the manufacturer (New England Biolabs, Beverly, Mass.). Up to 500 ng of vector was ligated to an appropriate amount of insert in 60 mM Tris, pH 7.6, 7 mM $MgCl_2$, 10 mM DTT, 1 mM ATP, and 400 units of $T_4$ ligase, and incubated at 14° C. overnight. These ligations were used to transform E. coli DH10B cells (Gibco-BRL, Grand Island, N.Y.) according to the manufacturer's protocol.

Figure 14:
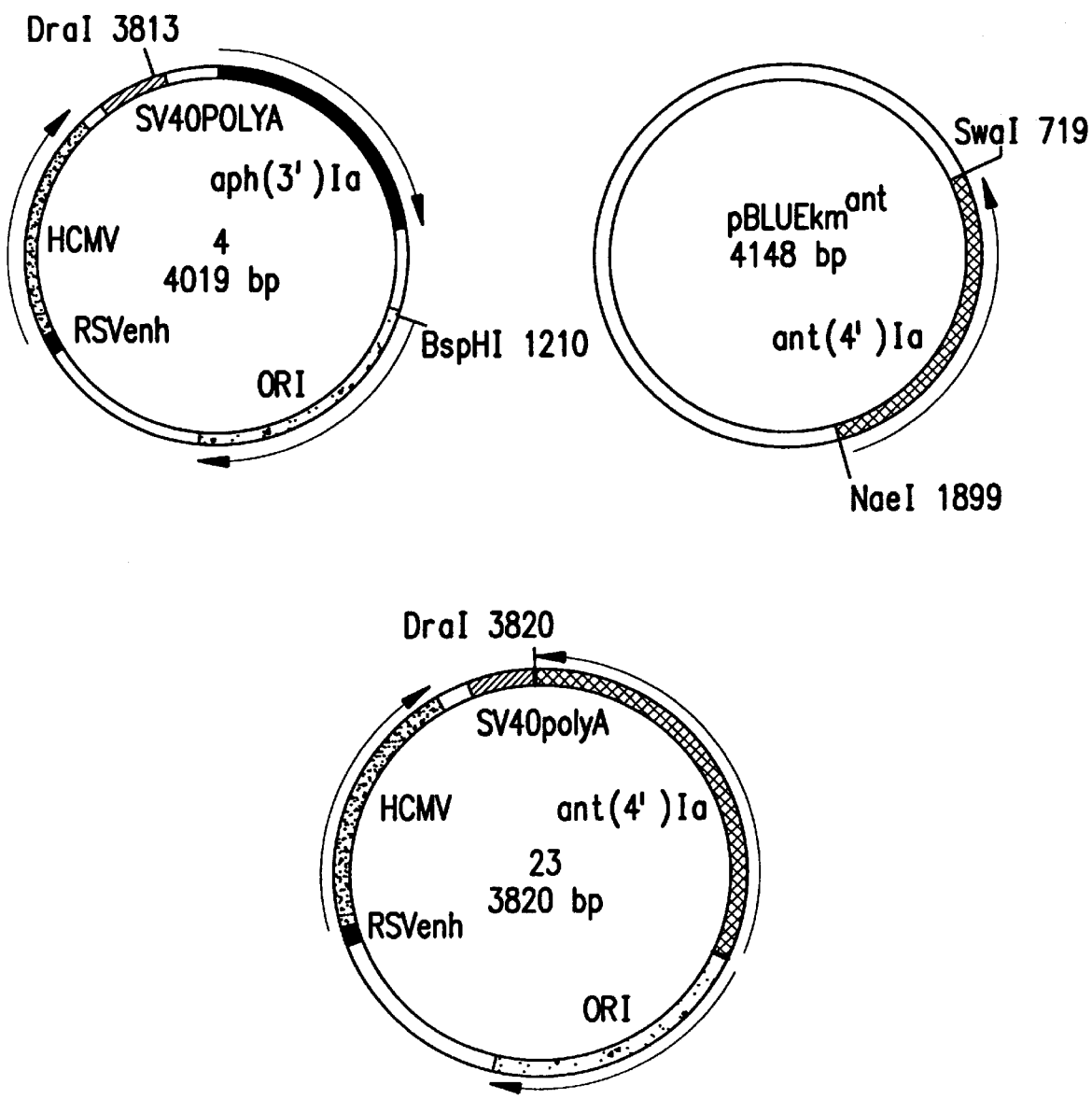
FIG. 14 shows construction of the plasmid 23 as described in Example 1. As detailed in the text, the aph(3')-Ia gene of the starting plasmid 4 was replaced with the chimeric ant(4')-Ia chimeric gene from pBLUEkm$^{ant}$. The β-lactamase gene remnant in the plasmid 4 is between the aph(3')-Ia gene and the BspHI site in the origin.

The ant(4')-Ia gene was ligated into plasmid 4 by CRC (FIG. 14). Plasmid 4 was cleaved with DraI and BspHI, and the 2.6 kb fragment generated by these enzymes was gel-purified. The 5' overhang generated by BspHI digestion was blunted with Klenow (Sambrook et al., 1989 Supra). The 1.2 kb ant(4')-Ia gene fragment was excised from pBLUEkm$^{ant}$ using NaeI and SwaI, which generate blunt ends, and the fragment was gel-purified. The desired fragments were subjected to CRC with bridge oligomers MPV73 and MPV92, and then the reaction was concentrated by precipitation and resuspended in 10 µl of TE (10 mM Tris, 7.6, 1 mM EDTA). One µl of the CRC reaction was used to transform E. coli DH10B cells (Gibco-BRL, Grand Island, N.Y.).

DNA Sequencing:

The Sequenase system (USB, Cleveland, Ohio) was employed for most of the sequencing performed. Approximately 50 ng of any given primer was used to prime a sequencing reaction. If a sequence could not be read by the Sequenase enzyme because of compressions, then the fmol® DNA sequencing system (Promega, Madison, Wis.) was used to resolve the discrepancies.

Cell Lines, Transfection Conditions, and Western Blots:

The human rhabdomyosarcoma cell line RD was maintained in MEM, alpha modification (JRH Biosciences, Lenexa, Kan.) supplemented with 10% fetal bovine serum, nonessential amino acids and sodium pyruvate. Cells were seeded into six-well plates, and transfected the next day with plasmid 19, plasmid 23, or plasmid 24 by the modified calcium phosphate method (Sambrook et al., 1989 Supra), or by lipofectamine according to the manufacturer's instructions (Gibco-BRL, Grand Island, N.Y.).

To determine if $HSVgD_2$ was produced by the cells, 48 hours after transfection the cells were lysed for Western blotting (Sambrook et al., 1989 Supra). Lysates were subjected to SDS-PAGE, and electroblotted to nitrocellulose. The blot was blocked with 0.5% Tween-20 and 5% nonfat dry milk in TBS, and incubated with the anti-$HSVgD_2$ monoclonal antibody Dl-6 diluted 1:250 in the same buffer. The blot was incubated with a secondary antibody, an anti-mouse IgG polyclonal antibody conjugated to alkaline phosphatase (Jackson Immunoresearch, Bar Harbor, Me.). Binding was then detected by incubation with substrates NBT/BCIP (Promega, Madison, Wis.).

Figure 16:
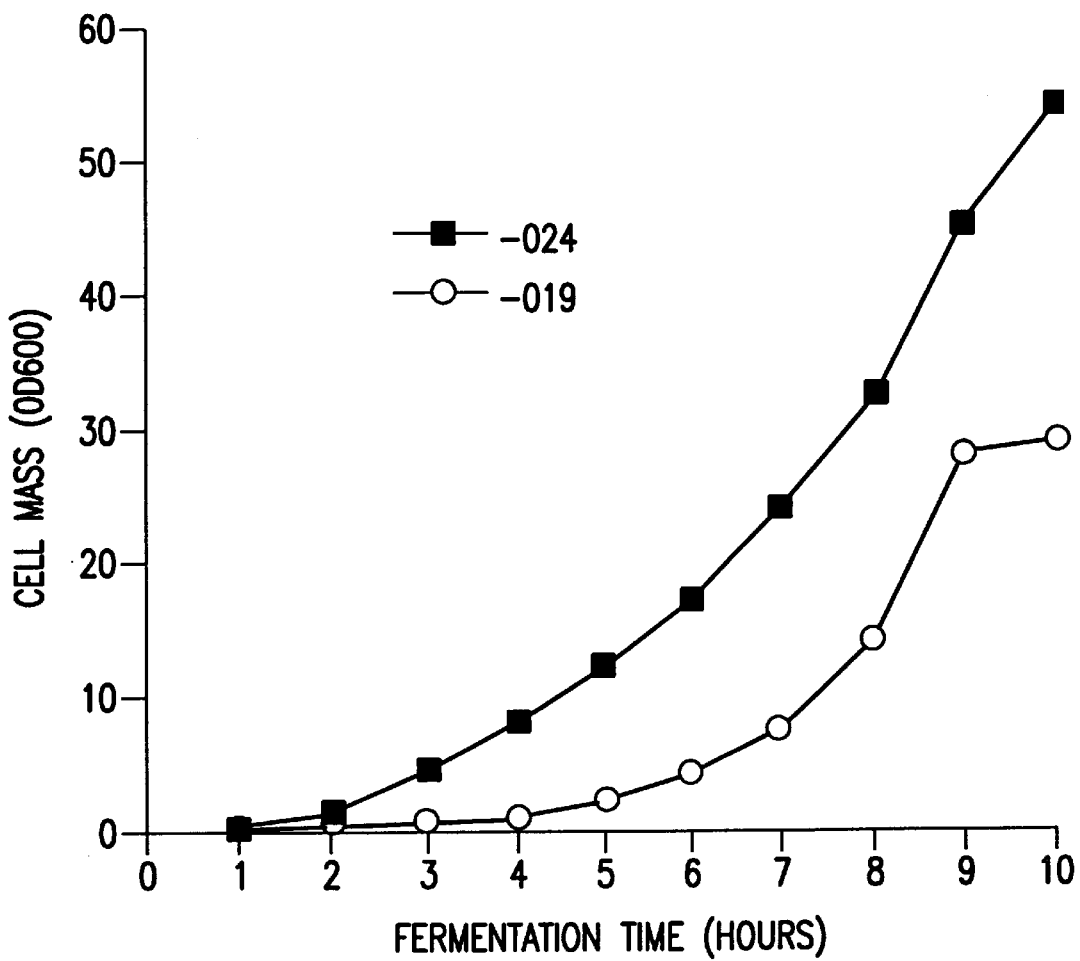
FIG. 16 shows results from experiments described in Example 1 relating to the growth of plasmid 19 and plasmid 24 in fermentation. Cell mass is measured against fermentation time for *E. coli* harboring either vector. FP5 is fermentation process 5.

Fermentations and Plasmid DNA Purification:

Fermentations were performed for E. coli DH10B containing either plasmid 19 or plasmid 24. The protocol used was fermentation process 5 (FP5). The growth profiles for either strain were very similar, and thus only one profile for each is shown in FIG. 16. Plasmid DNA was purified as described (Gayda 1995).

RESULTS AND DISCUSSION

Construction of the ant(4')-Ia Gene by PCR and CRC:

The ant(4')-Ia gene is derived from gram positive organisms. Its promoter, ribosome binding sites, and terminator are optimal for expression in such bacteria, but not for gram negative E. coli. The selectivity of gram negative promoters is due to the use of a single sigma factor versus the cascade of sigma factors required in gram positive organisms such as B. subtilis. In addition, gram negative bacterial ribosomes require that transcribed RNA contain specific signals for translation, which are lacking in RNA from gram positive organisms.

Initially, the coding region from the ant(4')-Ia gene was linked to the promoter and terminator from the aph(3')-Ia gene, which expresses well in E. coli. In addition, an Eco47III site within the ant(4')-Ia gene coding region needed to be eliminated for purposes of future cloning, but only a single base had to be altered, which did not change the protein sequence. PCR was used to individually amplify the aph(3')-Ia promoter, including the ribosome binding site, and the terminator sequences. The ant(4')-Ia gene coding region was likewise amplified in two pieces, with the antisense primer of the 5' fragment altering the Eco47III site.

The fragments were mixed in roughly equimolar amounts, with an excess of bridge oligomers to hybridize and join the fragments in the correct order. The fragments were subjected to CRC (FIG. 10B), and approximately 40% of the CRC reaction was then subjected to PCR. This second PCR reaction employed the two outermost primers, MPV37 and MPV44, which amplified across the entire length of the engineered gene. The PCR products were ligated into the pCR™3 vector, transformed into E. coli, and selected on LB ampicillin plates.

Of fifty clones selected for analysis, three were full length representations of the engineered ant(4')-Ia gene. One clone (pkm23) was fully sequenced, and found to be identical to the various input DNAs and with the correct junctions between each PCR fragment. This clone was selected for functional analysis.

The pCR™3 vector already contained a kanamycin resistance gene, so it was not possible to determine directly if ant(4')-Ia gene were functional in pkm23. The ant(4')-Ia gene insert of pkm23 was subcloned into pGEM11Zf+, a vector which only contains an ampicillin resistance gene. While the subcloning was successful, the bacteria containing pGEMkm$^{ant}$ plasmid grew only on plates containing ampicillin, not on plates containing kanamycin. Thus, the engineered ant(4')-Ia gene was not functional.

Reconstruction of the ant(4')-Ia Gene:

Closer examination of the translation initiation region of the engineered ant(4')-Ia gene suggested that it was not functional because it was not translated correctly in E. coli. Translation initiation regions in E. coli genes are characterized by a purine-rich ribosome binding sequence, called the Shine-Dalgarno box, followed 5 to 15 bases downstream by the translation initiation codon, usually the first ATG of the coding sequence. One of the many differences between gram negative and gram positive organisms is that the former almost always use ATG as the start codon, but the latter use ATG or GTG. In fact, the GTG codon is poorly recognized as the initiation codon by gram negative bacteria.

The engineered ant(4')-Ia gene contains a Shine-Dalgarno box from the aph(3')-Ia promoter, but it is followed by two potential start codons from the ant(4')-Ia coding sequence: the in-frame GTG and an out-of-frame ATG that are 5 and 9 bases downstream, respectively (FIG. 11). Only translation from the GTG would give rise to a functional enzyme, but it is unlikely to be recognized as the start codon by E. coli ribosomes.

Figure 13B:
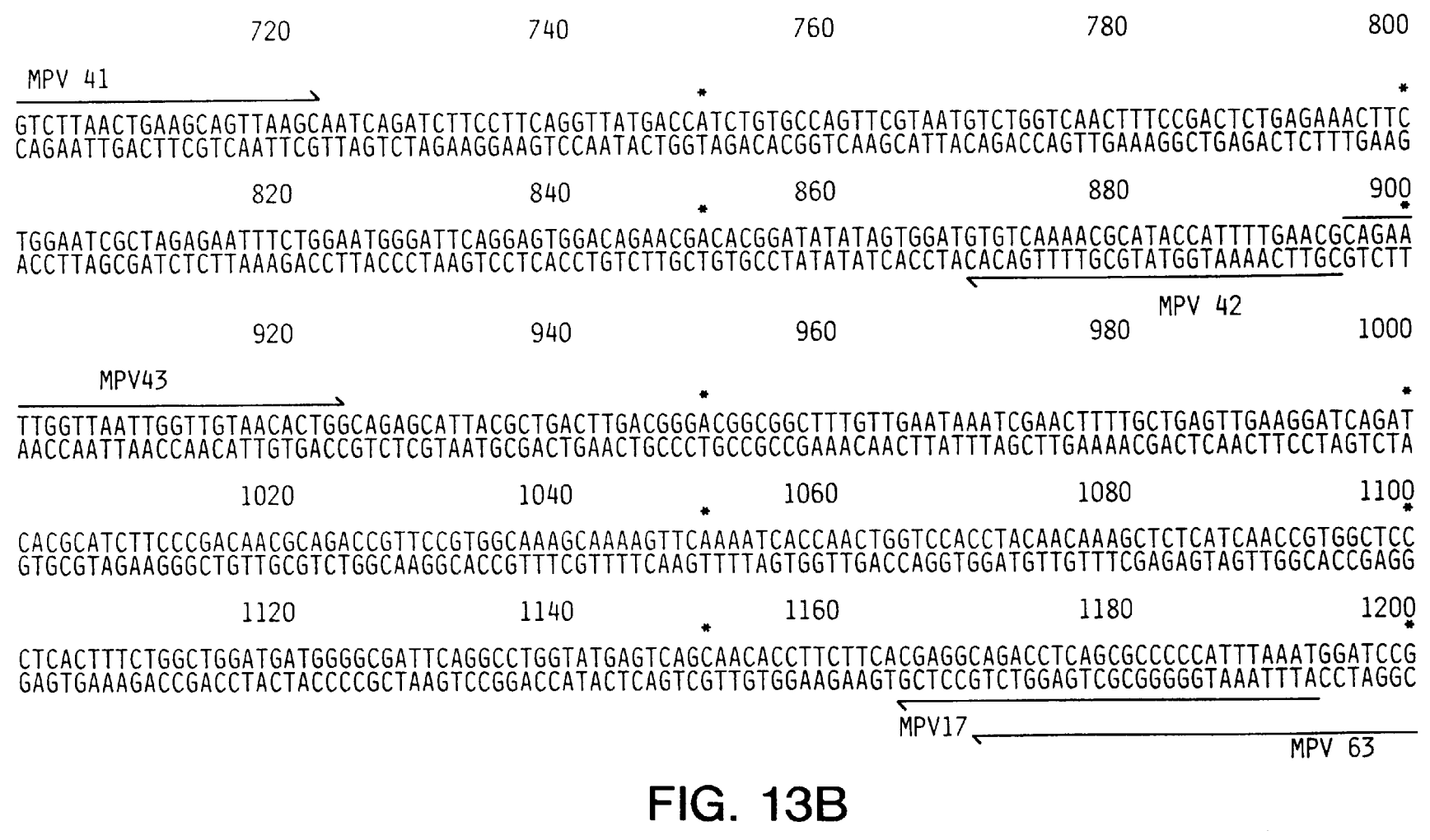

Based on the above analysis, the translation initiation region was altered, from GTG AAT GGA (SEQ ID NO:3) to ATG AAC GGA (SEQ ID NO:4). Changing the bold-faced bases does not alter the protein sequence. Again, a combination of PCR and CRC was employed to generate these mutations, as detailed in FIGS. 12A and 12B. The pGEMk-M$^{ant}$ plasmid served as template, in which the promoter was amplified in one reaction, and the coding region and terminator in another reaction. The sense primer used to amplify the coding region and terminator incorporated the desired nucleotide changes. The PCR fragments were then linked by CRC, and the products were amplified by a second round of PCR using the outermost primers to amplify the entire gene. The final PCR product was cleaved at unique sites on the 5' and 3' ends, and cloned directly into pBluescript which only carries an ampicillin resistance gene. The ligations were transformed into E. coli, and grown on plates containing kanamycin. Twenty-two colonies were obtained, and three were sequenced in the junction region between the promoter and coding region. All three had the corrected first and second codons. The ant(4')-Ia gene of one of the three clones was then sequenced, and found to be otherwise identical to the pGEMkm$^{ant}$ template (see FIG. 13). This clone is designated pBLUEkm$^{ant}$ and it contains an insert of 1200 bp, with an open reading frame of 254 amino acids, flanked by a 5' promoter sequence of 130 bp and a 3' terminator of 308 bp.

Aminoglycoside Sensitivity of E. coli Carrying ant(4')-Ia:

A sensitivity/resistance profile to seven of the most frequently prescribed aminoglycosides was determined for E. coli carrying either the ant(4')-Ia gene or the aph(3')-Ia gene. The pBLUEkm$^{ant}$ and pUC4K plasmids were transformed into E. coli DH10B, a strain which carries a streptomycin resistance marker. The transformed strains and the host strain were tested against a series of aminoglycosides to determine their minimum inhibitory concentrations (MIC). Results are shown in Table 2, with MICs shown in µg/ml, and resistance or sensitivity indicated. All strains are resistant to streptomycin as expected, but neither the ant(4')-Ia gene nor the aph(3')-Ia gene is expected to confer resistance to this antibiotic (Shaw et al., 1993). The E. coli strain alone is sensitive to the remaining antibiotics, providing a baseline of comparison for the bacteria carrying the plasmids with the ant(4')-Ia gene or the aph(3')-Ia gene. The data show that the ant(4')-Ia gene confers resistance to kanamycin, neomycin, and tobramycin, while the aph(3')-Ia gene confers resistance to kanamycin, neomycin, tobramycin, gentamicin and netilmicin. The most significant difference between the two genes is that the ant(4')-Ia gene is sensitive to gentamicin, an antibiotic that is still the first course of treatment for gram negative infections. Thus, the engineered ant(4')-Ia gene fulfills the requirement that it display a narrower range of activity against aminoglycosides, and should be safer for use in humans.

Replacement of the aph(3')-Ia Gene in plasmid 4 with ant(4')-Ia:

The ant(4')-Ia gene was cloned by CRC into plasmid 4, to replace the aph(3')-Ia gene contained in this vector backbone. Plasmid 4 was cleaved with DraI and BspHI, which eliminates the aph(3')-Ia gene and a remnant of the β-lactamase gene left in the plasmid during its original construction. The DraI site is at the 3' end of the SV40 polyadenylation signal. Cleavage at this site removes 42 bases at one end of the element, which is not expected to affect its function. The modified clinical vector backbone resulting from this work is designated plasmid 23. Restriction analysis of plasmid 23 and sequencing of the junctions between the plasmid 4 fragment and ant(4')-Ia fragment in plasmid 23 verified that the fragments went together in the desired orientation.

In plasmid 4, aph(3')-Ia transcription was directed toward the origin. The terminator of aph(3')-Ia is rho-dependent, and rho-dependent terminators can allow a low level of readthrough transcription to occur (Darnell, J. et al., *Molecular Cell Biology*, 1986, which is incorporated herein by reference, and Miller, J. H. et al., The Operon 1980 which is incorporated herein by reference), in this case originating from the aph(3')-Ia promoter. The readthrough could result in additional RNA II transcription from the origin. Plasmid replication is, in part, a function of the binding of RNA I to RNA II (Kues, U. et al., *Microbiol. Rev.* 1989, 53:491–516, which is incorporated herein by reference), and the extra RNA II transcription might be expected to result in lower plasmid copy number per cell. To get around this potential problem, the ant(4')-Ia gene was ligated into plasmid 4 so that its transcription is directed away from the origin.

Figure 15A:
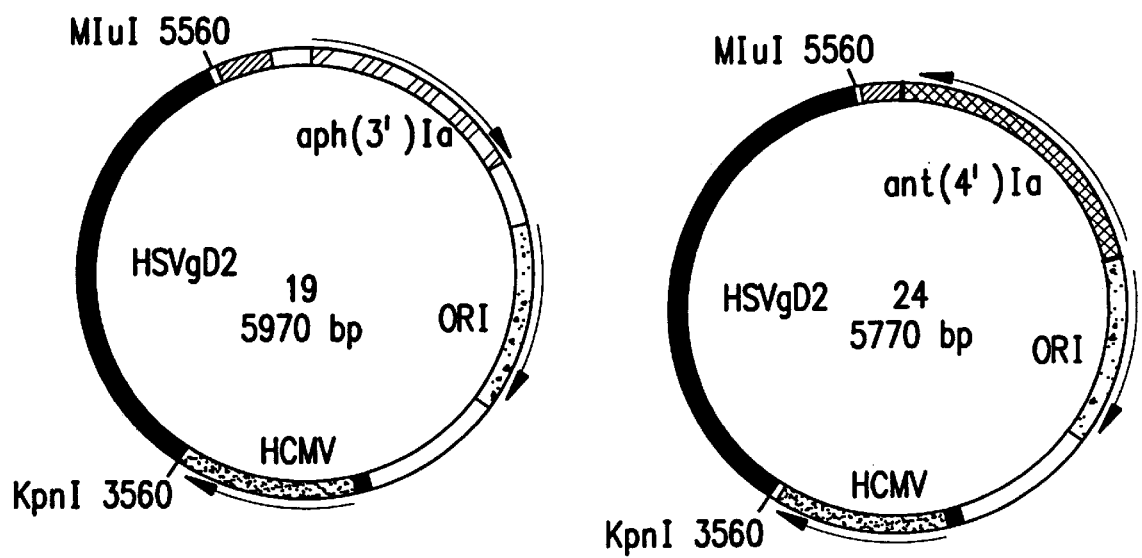
FIGS. 15A and 15B show expression of the HSV gene HSVgD$_2$ in cells transfected with the plasmid 24 as described in Example 1.

Expression of HSVgD$_2$ from plasmid 19 and plasmid 24:

When plasmid 23 was constructed, a small portion of the SV40 polyadenylation signal was deleted as described above. This deletion did not include the AATAAA sequence, or the GT-rich region required for efficient polyadenylation, but it remained possible that this deletion could adversely affect expression of the eukaryotic gene unit. To evaluate this concern, the HSVgD$_2$ gene from plasmid 19 was cloned into plasmid 23, to yield plasmid 24 (FIG. 15A). The only differences between plasmid 19 and plasmid 24 are the polyadenylation signals, and the aph(3')-Ia and ant(4')-Ia genes, respectively.

Figure 15B:
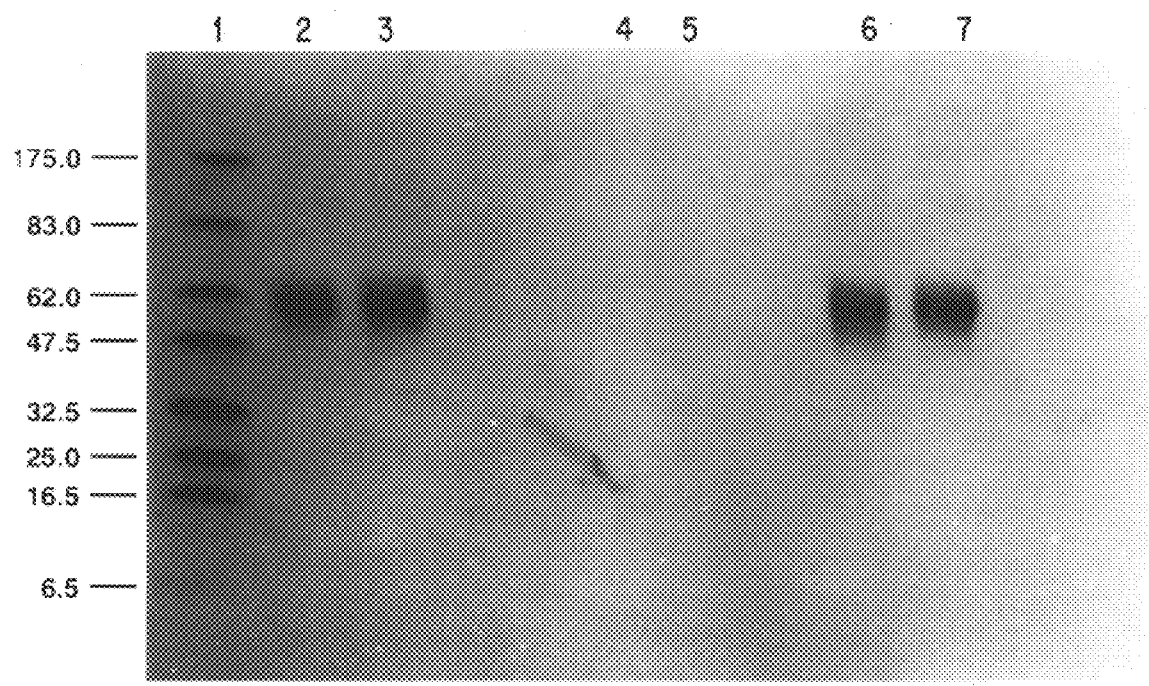

Expression studies were performed, in which RD cells were transfected with either plasmid 19, plasmid 23 or plasmid 24. Results are shown in FIG. 15B. Cells transfected with either of the vectors containing HSVgD$_2$ produce substantial amounts of the 55 kilodalton HSVgD$_2$ protein as detected by Western blot, while the lanes representing the control plasmid are negative. These data suggest that the small deletion in the SV40 polyadenylation signal does not adversely affect eukaryotic gene expression from the vector. In addition, the presence of the ant(4')-Ia gene coding sequence in the vector does not appear to affect expression from the eukaryotic promoter.

Fermentation and Plasmid Yields of Bacteria Containing plasmid 19 or plasmid 24:

To determine if the presence of the ant(4')-Ia gene coding sequence in a plasmid vector backbone would influence production of plasmid DNA, three fermentations of plasmid 24 were compared with two fermentations of plasmid 19. Each plasmid vector is in *E. coli* strain DH10B, and the same fermentation and DNA purification protocols were performed for each strain.

Representative growth curves for the two bacterial strains are shown in FIG. 16. The plasmid 24 strain grows much more rapidly than the plasmid 19 strain, and reaches nearly twice the OD$_{600}$ after ten hours of fermentation. The plasmid DNA yields for each strain were also compared (Table 3). More plasmid 24 DNA was produced than plasmid 19, but the amounts are proportional to the cell yield. Thus, bacteria containing plasmid 24 or plasmid 19 produce similar amounts of plasmid DNA, but because the plasmid 24 strain grows so much better, the yield of DNA from fermentation has improved substantially.

It is likely that the growth advantage seen with plasmid 24 is due to the biochemical activities of the ANT(4')-IA enzyme when compared with those of the APH(3')-IA enzyme. The ATP used as a phosphate donor by APH(3')-IA is limited in concentration in growing cells. Given the ability of APH(3')-IA to phosphorylate a wide range of cellular substrates, including kanamycin and water, bacteria harboring this enzyme to grow more slowly due to futile cycles of ATP generation followed by APH(3')-Ia mediated ATP breakdown.

ANT(4')-IA enzyme may have additional cellular activities beyond conferring drug resistance, including a positive effect on cell growth. It is well known that cell growth is controlled by the levels of several global growth regulators, including cyclic AMP (cAMP), leucine and glutamine. In particular, cAMP is a negative global growth regulator, in that high cellular levels of this metabolite are associated with low growth rate, while low cAMP levels are associated with a high growth rate. Since ANT(4')-IA enzyme acts by cleaving nucleotides, cAMP may serve as a substrate for the enzyme.

To assess the cAMP phosphodiesterase activity in *E. coli* alone, and in *E. coli* with plasmids carrying either aph(3')-Ia or ant(4')-Ia an experiment was done. *E. coli* with the ant(4')-Ia gene possess 320-fold more cAMP phosphodiesterase activity than *E. coli* alone, and 400-fold more activity than *E. coli* bearing aph(3')-Ia. Lower intracellular levels of cAMP may account for the improved cellular growth rate seen in *E. coli* bearing ant(4')-Ia. That is, the elevated cAMP phosphodiesterase activity seen in *E. coli* that expresses ANT(4')-IA enzyme, may leads to lower levels of cAMP which could account for higher cellular growth.

The beneficial biochemical effects of the chimeric ant(4')-Ia gene could be conferred to host cells in either of two ways. The ant(4')-Ia gene could be supplied on a plasmid, as in the case of plasmid 24. Alternatively, the ant(4')-Ia gene could be integrated into the chromosomal DNA of cells. Two examples follow. First, to generate a mammalian cell line with the ant(4')-Ia gene integrated into the chromosome, one would transfect cells with a plasmid containing ant(4')-Ia, and select for cell clones stably resistant to neomycin (neomycin, but not kanamycin, is toxic to mammalian cells, and as shown previously, ant-(4')-Ia confers resistance to neomycin). Second, an *E. coli* strain with the ant(4')-Ia gene integrated into the chromosome could be generated by homologous recombination. In this case, one would insert the ant(4')-Ia gene into the center of 1–2 kb of cloned *E. coli* DNA, and use the resulting linear fragment to transform *E. coli* (C. Satishchandran, et al., 1991 *J. Bacteriol.* 172:4489–4496 incorporated herein). Kanamycin-resistant strains would be selected for and analyzed molecularly to show that the desired recombination event occurred.

CONCLUSIONS

A hybrid kanamycin resistance gene which utilizes the *E. coli* aph(3')-Ia promoter and terminator to control expression of the ant(4')-Ia coding region is described. The first and second codons of the engineered gene have been altered to ensure efficient expression of the gene. When the sensitivity spectrum of *E. coli* strains carrying ant(4')-Ia was compared with that of strains carrying aph(3')-Ia, ant(4')-Ia conferred resistance only to kanamycin, neomycin and tobramycin, while aph(3')-Ia conferred resistance to kanamycin, neomycin, tobramycin, netilmicin, and gentamicin. Thus, the engineered gene has a more restricted range of activity and represents a significant safety improvement relative to clinical vectors which employ the aph(3')-Ia gene. The vector backbones with the ant(4')-Ia gene support good expression from the eukaryotic promoter contained in the backbone. Finally, the presence of the ant(4')-Ia gene in the backbone is a manufacturing improvement, in that bacteria bearing plasmid 23-derived vectors grow significantly better and consequently produce more DNA.

TABLE 1

PRIMERS AND OLIGOMERS

SEQUENCE OF PRIMERS (5' TO 3')

PCR PRIMERS

| | | |
|---|---|---|
| MPV37 | GGCCGGCCGGGGAAAGCCACGTTGTGTCTC | (SEQ ID NO:5) |
| MPV38 | AACACCCCTTGTATTACTGTTTATGTAAG | (SEQ ID NO:6) |
| MPV39 | GTGAATGGACCAATAATAATGACTAGAG | (SEQ ID NO:7) |
| MPV40 | CGCGCTCGTCGTATAACAGATGCG | (SEQ ID NO:8) |
| MPV41 | TCGGTCTTAACTGAAGCAGTTAAGC | (SEQ ID NO:9) |
| MPV42 | CGTTCAAAATGGTATGCGTTTTGACAC | (SEQ ID NO:10) |
| MPV43 | CAGAATTGGTTAATTGGTTGTAACACTG | (SEQ ID NO:11) |
| MPV44 | ATTTAAATGGGGCGCTGAGGTCTGCCTCG | (SEQ ID NO:12) |
| MPV62 | ATGAACGGACCAATAATAATGACTAGAGAAGAAAG | (SEQ ID NO:13) |
| MPV63 | CGGGATCCATTTAAATGGGGCGCTGAGGTCTG | (SEQ ID NO:14) |
| MPV64 | GCTCTAGAGGCCGGCCGGGGAAAGCCACG | (SEQ ID NO:15) |

BRIDGE OLIGOMERS

| | | |
|---|---|---|
| MPV45 | CAGTAATACAAGGGGTGTTGTGAATGGACCAATAATAATG | (SEQ ID NO:16) |
| MPV46 | GTTATACGACGAGCGCGTCGGTCTTAACTGAAGCAG | (SEQ ID NO:17) |
| MPV47 | CGCATACCATTTTGAACGCAGAATTGGTTAATTGGTTG | (SEQ ID NO:18) |
| MPV67 | CAGTAATACAAGGGGTGTTATGAACGGACCAATAATAATG | (SEQ ID NO:19) |
| MPV73 | CACAACGTGGCTTTCCCCGGCCCATGACCAAAATCCCTTAACGTGAG | (SEQ ID NO:20) |
| MPV92 | CAGGGGGAGGTGTGGGAGGTTTTTTAAATGGGGCGCTGAGGTCTGCC | (SEQ ID NO:21) |

TABLE 2

Spectrum of Activity of ANT(4')-IA and APH(3')-IA Against Aminoglycosides

| Aminoglycoside | DH10B | DH10B/pBLUEkm$^{ant}$ | DH10B/pUC4K |
|---|---|---|---|
| kanamycin | 1.0 S | 32 R | 32 R |
| neomycin | 0.5 S | 32 R | 32 R |
| tobramycin | 1.0 S | 16 R | 8 R |
| gentamicin | 0.5 S | 0.25 S | 5 R |
| netilmicin | 0.12 S | 0.25 S | 25 R |
| streptomycin | 128 R | 128 R | 128 R |
| spectinomycin | 4.0 S | 4.0 S | 4.0 S |

TABLE 3

Yields of plasmid 19 and plasmid 24 DNA After Fermentation

| | plasmid 19 | plasmid 24 | 24/19 |
|---|---|---|---|
| Cells (g/l) | 46 | 86 | 1.86 |
| Plasmid DNA (mg/l) | 13 | 22 | 1.69 |

We claim:

1. A method of synthesizing a composite nucleic acid molecule comprising the steps of:

a) heating a first double-stranded nucleic acid molecule and a second double-stranded nucleic acid molecule at a denaturing temperature;

b) forming a mixture comprising said first denatured nucleic acid molecule, said second denatured nucleic acid molecule, a bridging oligonucleotide and a thermostable ligase,
   wherein said denatured nucleic acid molecules each consist of a first strand and a second strand complementary thereto, and
   wherein said bridging oligonucleotide comprises, from 5' to 3', a 10–40 nucleotide sequence which is complementary to a nucleotide sequence on the 5' end of the first strand of said first nucleic acid molecule and a 10–40 nucleotide sequence which is complementary to a nucleotide sequence on the 3' end of the first strand of said second nucleic acid molecule;

c) maintaining said mixture at an annealing temperature, wherein said bridging oligonucleotide hybridizes to sequences on the first strands of both said first and second nucleic acid molecule, thereby orienting said first and second molecules adjacent to each other, and wherein said thermostable ligase ligates either said 3' end of said first nucleic acid molecule to said 5' end of said second nucleic acid molecule or said 5' end of said first nucleic acid molecule to said 3' end of said second nucleic acid molecule to form a first strand of said composite nucleic acid molecule hybridized to said bridging oligonucleotide;

d) maintaining said mixture at a denaturing temperature, wherein said bridging oligonucleotide dissociates from said first strand of said composite nucleic acid molecule; and e) maintaining said mixture at an annealing temperature, wherein said first strand of said composite nucleic acid molecule hybridizes to complementary strands of said first nucleic acid molecules and said second nucleic acid molecule, wherein said thermostable ligase ligates the end of said complementary strand of said first nucleic acid molecules to the end of said complementary strand of second nucleic acid molecule to form a second strand of said composite nucleic acid molecule.

2. The method of claim 1 wherein the concentration of thermostable ligase in said mixture is 1–20 units/100 ul reaction.

3. The method of claim 2 wherein the concentration of thermostable ligase in said mixture is 5 units/100 ul reaction.

4. The method of claim 1 wherein the nucleic acid molecules are DNA and the ratio of the amount of bridging oligonucleotide in said mixture to the amount of DNA present for ligation is 1 to 1.

5. A method of ligating a plurality of nucleic acid molecules comprising the steps of the method of claim 1 wherein laid mixture comprises a plurality of nucleic acid molecules and a plurality of bridging oligonucleotides.

6. The method of claim 5 wherein said plurality of nucleic acid molecules comprises a vector and a DNA molecule to be inserted therein.

7. The method of claim 5 wherein said plurality of nucleic acid molecules comprise a plurality of polymerase chain reaction products.

8. The method of claim 7 wherein said mixture further comprises a non-strand displacing heat stable DNA polymerase.

9. A method of synthesizing a composite nucleic acid molecule comprising the steps of:
  a) forming a mixture comprising a first denatured nucleic acid molecule, a second denatured nucleic acid molecule, a bridging oligonucleotide and a thermostable ligase,
    wherein said denatured nucleic acid molecules each consist of first and second complementary strands, and
    wherein said bridging oligonucleotide comprises, from 5' to 3', a 10–40 nucleotide sequence which is complementary to a nucleotide sequence on the 5' end of the first strand of said first nucleic acid molecule and a 10–40 nucleotide sequence which is complementary to a nucleotide sequence on the 3' end of the first strand of said second nucleic acid molecule;
  b) heating said mixture at an annealing temperature, wherein said bridging oligonucleotide hybridizes to sequences on the first strands of both said first and second nucleic acid molecules or to sequences on the second strands of both said first and second nucleic acid molecules, thereby orienting said first and second nucleic acid molecules adjacent to each other, and wherein said thermostable ligase ligates either said 3' end of said first nucleic acid molecule to said 5' end of said second nucleic acid molecule or said 5' end of said first nucleic acid molecule to said 3' end of said second nucleic acid molecule to form a first strand of said composite nucleic acid molecule hybridized to said bridging oligonucleotide;
  c) heating said mixture at a denaturing temperature, wherein said bridging oligonucleotide dissociates from said first strand of said composite nucleic acid molecule; and
  d) heating said mixture at an annealing temperature, wherein said first strand of said composite nucleic acid molecule hybridizes to complementary strands of said first nucleic acid molecules and said second nucleic acid molecule, wherein said thermostable ligase ligates the end of said complementary strand of said first nucleic acid molecules to the end of said complementary strand of second nucleic acid molecule to form a second strand of said composite nucleic acid molecule.

10. The method of claim 9 wherein the concentration of thermostable ligase in said mixture is 1 to 20 units/100 μl reaction.

11. The method of claim 10 wherein the concentration of thermostable ligase in said mixture is 5 units/100 μl reaction.

12. The method according to claim 9, wherein said mixture comprises a plurality of nucleic acid molecules which comprise vectors and DNA molecules to be inserted therein.

13. The method according to claim 9, wherein said nucleic acid molecules are DNA and said mixture further comprises a non-strand displacing heat stable DNA polymerase.

14. A method of synthesizing a composite nucleic acid molecule comprising the steps of:
  a) forming a mixture comprising a denatured double-stranded first nucleic acid molecule, a second nucleic acid molecule, a bridging oligonucleotide, and a thermostable ligase,
    wherein said bridging oligonucleotide comprises, from 5' to 3', a 10–40 nucleotide sequence which is complementary to a nucleotide sequence on the 5' end of the first strand of said first nucleic acid molecule and a 10–40 nucleotide sequence which is complementary to a nucleotide sequence on the 3' end of the first strand of said second nucleic acid molecule;
  b) heating said mixture at an annealing temperature, wherein said bridging oligonucleotide hybridizes to sequences on the first strand of said first nucleic acid molecule and to sequences on said second nucleic acid molecule and wherein said thermostable ligase ligates said 5' end of said strand of said first nucleic acid molecule to said 3' end of said second nucleic acid molecule to form a first strand of said composite nucleic acid molecule hybridized to said bridging oligonucleotide;
  c) dissociating said bridging oligonucleotide from said first strand of said composite nucleic acid molecule; and
  d) heating said mixture at an annealing temperature, wherein said first strand of said composite nucleic acid molecule hybridizes to complementary strands of said first nucleic acid molecule to form a second strand of said composite nucleic acid molecule.

15. The method according to claim 9, wherein said mixture comprises a plurality of bridging oligonucleotides and a plurality of nucleic acid molecules which comprise a plurality of polymerase chain reaction products.

16. The method according to claim 1, wherein steps c), d) and e) are repeated a plurality of times.

17. A method according to claim 1, said method further comprising the step of f) amplifying said composite nucleic acid molecule by polymerase chain reaction using the two outermost primers, thereby amplifying across the entire length of the composite nucleic acid molecule.

18. The method according to claim 1, wherein said mixture further comprises dNTPs.

19. The method according to claim 9, wherein said mixture further comprises dNTPs.

* * * * *

UNITED STATES PATENT AND TRADEMARK OFFICE
CERTIFICATE OF CORRECTION

PATENT NO. : 6,143,527
DATED : November 7, 2000
INVENTOR(S) : Catherine J. Pachuk It is certified that error appears in the above-identified patent and that said Letters Patent is hereby corrected as shown below:

Col. 6, line 63, replace " "DNA LIGASE with -- " DNA LIGASE" -- .

Col. 7, line 22, replace "is" with -- 1s -- .

Col. 7, line 29, replace "is" with -- 1s -- .

Col. 7, line 40, replace "is" with -- 1s -- .

Col. 7, line 60, replace "is" with -- 1s -- .

Col. 7, line 63, replace "is" with -- 1s -- .

Col. 10, line 64, delete the extra word "of"

Col. 14, line 45, replace "0.0010" with -- 0.001% -- .

Signed and Sealed this

First Day of May, 2001

Attest:

NICHOLAS P. GODICI

Attesting Officer     Acting Director of the United States Patent and Trademark Office

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1200 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 131..892

(xi) SEQUENCE DESCRIPTION: SEQ ID NO:1:

```
GCTCTAGAGG CCGGCCGGGG AAAGCCACGT TGTGTCTCAA AATCTCTGAT GTTACATTGC        60

ACAAGATAAA AATATATCAT CATGAACAAT AAAACTGTCT GCTTACATAA ACAGTAATAC       120

AAGGGGTGTT ATG AAC GGA CCA ATA ATA ATG ACT AGA GAA GAA AGA ATG         169
           Met Asn Gly Pro Ile Ile Met Thr Arg Glu Glu Arg Met
             1               5                  10

AAG ATT GTT CAT GAA ATT AAG GAA CGA ATA TTG GAT AAA TAT GGG GAT         217
Lys Ile Val His Glu Ile Lys Glu Arg Ile Leu Asp Lys Tyr Gly Asp
 15                  20                  25

GAT GTT AAG GCT ATT GGT GTT TAT GGC TCT CTT GGT CGT CAG ACT GAT         265
Asp Val Lys Ala Ile Gly Val Tyr Gly Ser Leu Gly Arg Gln Thr Asp
 30                  35                  40                  45

GGG CCC TAT TCG GAT ATT GAG ATG ATG TGT GTC ATG TCA ACA GAG GAA         313
Gly Pro Tyr Ser Asp Ile Glu Met Met Cys Val Met Ser Thr Glu Glu
                 50                  55                  60

GCA GAG TTC AGC CAT GAA TGG ACA ACC GGT GAG TGG AAG GTG GAA GTG         361
Ala Glu Phe Ser His Glu Trp Thr Thr Gly Glu Trp Lys Val Glu Val
             65                  70                  75

AAT TTT GAT AGC GAA GAG ATT CTA CTA GAT TAT GCA TCT CAG GTG GAA         409
Asn Phe Asp Ser Glu Glu Ile Leu Leu Asp Tyr Ala Ser Gln Val Glu
         80                  85                  90

TCA GAT TGG CCG CTT ACA CAT GGT CAA TTT TTC TCT ATT TTG CCG ATT         457
Ser Asp Trp Pro Leu Thr His Gly Gln Phe Phe Ser Ile Leu Pro Ile
     95                 100                 105

TAT GAT TCA GGT GGA TAC TTA GAG AAA GTG TAT CAA ACT GCT AAA TCG         505
Tyr Asp Ser Gly Gly Tyr Leu Glu Lys Val Tyr Gln Thr Ala Lys Ser
110                 115                 120                 125

GTA GAA GCC CAA ACG TTC CAC GAT GCG ATT TGT GCC CTT ATC GTA GAA         553
Val Glu Ala Gln Thr Phe His Asp Ala Ile Cys Ala Leu Ile Val Glu
                130                 135                 140

GAG CTG TTT GAA TAT GCA GGC AAA TGG CGT AAT ATT CGT GTG CAA GGA         601
Glu Leu Phe Glu Tyr Ala Gly Lys Trp Arg Asn Ile Arg Val Gln Gly
            145                 150                 155

CCG ACA ACA TTT CTA CCA TCC TTG ACT GTA CAG GTA GCA ATG GCA GGT         649
Pro Thr Thr Phe Leu Pro Ser Leu Thr Val Gln Val Ala Met Ala Gly
        160                 165                 170

GCC ATG TTG ATT GGT CTG CAT CAT CGC ATC TGT TAT ACG ACG AGC GCG         697
Ala Met Leu Ile Gly Leu His His Arg Ile Cys Tyr Thr Thr Ser Ala
    175                 180                 185

TCG GTC TTA ACT GAA GCA GTT AAG CAA TCA GAT CTT CCT TCA GGT TAT         745
Ser Val Leu Thr Glu Ala Val Lys Gln Ser Asp Leu Pro Ser Gly Tyr
190                 195                 200                 205
```

```
GAC CAT CTG TGC CAG TTC GTA ATG TCT GGT CAA CTT TCC GAC TCT GAG        793
Asp His Leu Cys Gln Phe Val Met Ser Gly Gln Leu Ser Asp Ser Glu
            210                 215                 220

AAA CTT CTG GAA TCG CTA GAG AAT TTC TGG AAT GGG ATT CAG GAG TGG        841
Lys Leu Leu Glu Ser Leu Glu Asn Phe Trp Asn Gly Ile Gln Glu Trp
                225                 230                 235

ACA GAA CGA CAC GGA TAT ATA GTG GAT GTG TCA AAA CGC ATA CCA TTT        889
Thr Glu Arg His Gly Tyr Ile Val Asp Val Ser Lys Arg Ile Pro Phe
                    240                 245                 250

TGA ACGCAGAATT GGTTAATTGG TTGTAACACT GGCAGAGCAT TACGCTGACT             942
 *

TGACGGGACG GCGGCTTTGT TGAATAAATC GAACTTTTGC TGAGTTGAAG GATCAGATCA     1002

CGCATCTTCC CGACAACGCA GACCGTTCCG TGGCAAAGCA AAAGTTCAAA ATCACCAACT     1062

GGTCCACCTA CAACAAAGCT CTCATCAACC GTGGCTCCCT CACTTTCTGG CTGGATGATG     1122

GGGCGATTCA GGCCTGGTAT GAGTCAGCAA CACCTTCTTC ACGAGGCAGA CCTCAGCGCC     1182

CCCATTTAAA TGGATCCG                                                   1200

(2) INFORMATION FOR SEQ ID NO:2:

(i) SEQUENCE CHARACTERISTICS:
        (A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Gly Pro Ile Ile Met Thr Arg Glu Glu Arg Met Lys Ile Val
 1               5                  10                  15

His Glu Ile Lys Glu Arg Ile Leu Asp Lys Tyr Gly Asp Asp Val Lys
                20                  25                  30

Ala Ile Gly Val Tyr Gly Ser Leu Gly Arg Gln Thr Asp Gly Pro Tyr
            35                  40                  45

Ser Asp Ile Glu Met Met Cys Val Met Ser Thr Glu Glu Ala Glu Phe
        50                  55                  60

Ser His Glu Trp Thr Thr Gly Glu Trp Lys Val Glu Val Asn Phe Asp
65                  70                  75                  80

Ser Glu Glu Ile Leu Leu Asp Tyr Ala Ser Gln Val Glu Ser Asp Trp
                85                  90                  95

Pro Leu Thr His Gly Gln Phe Phe Ser Ile Leu Pro Ile Tyr Asp Ser
            100                 105                 110

Gly Gly Tyr Leu Glu Lys Val Tyr Gln Thr Ala Lys Ser Val Glu Ala
        115                 120                 125

Gln Thr Phe His Asp Ala Ile Cys Ala Leu Ile Val Glu Glu Leu Phe
    130                 135                 140

Glu Tyr Ala Gly Lys Trp Arg Asn Ile Arg Val Gln Gly Pro Thr Thr
145                 150                 155                 160

Phe Leu Pro Ser Leu Thr Val Gln Val Ala Met Ala Gly Ala Met Leu
                165                 170                 175

Ile Gly Leu His His Arg Ile Cys Tyr Thr Thr Ser Ala Ser Val Leu
            180                 185                 190

Thr Glu Ala Val Lys Gln Ser Asp Leu Pro Ser Gly Tyr Asp His Leu
        195                 200                 205

Cys Gln Phe Val Met Ser Gly Gln Leu Ser Asp Ser Glu Lys Leu Leu
    210                 215                 220
```

```
Glu Ser Leu Glu Asn Phe Trp Asn Gly Ile Gln Glu Trp Thr Glu Arg
225                 230                 235                 240

His Gly Tyr Ile Val Asp Val Ser Lys Arg Ile Pro Phe
                245                 250
```

(2) INFORMATION FOR SEQ ID NO:3:

(i) SEQUENCE CHARACTERISTICS:
        (A) LENGTH: 9 base pairs
        (B) TYPE: nucleic acid
        (C) STRANDEDNESS: both
        (D) TOPOLOGY: both (ii) MOLECULE TYPE: DNA (xi) SEQUENCE DESCRIPTION: SEQ ID NO:3:

GTGAATGGA                                                                   9

(2) INFORMATION FOR SEQ ID NO:4:

(i) SEQUENCE CHARACTERISTICS:
        (A) LENGTH: 9 base pairs
        (B) TYPE: nucleic acid
        (C) STRANDEDNESS: both
        (D) TOPOLOGY: both (ii) MOLECULE TYPE: DNA (xi) SEQUENCE DESCRIPTION: SEQ ID NO:4:

ATGAACGGA                                                                   9

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GGCCGGCCGG GGAAAGCCAC GTTGTGTCTC                            30

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AACACCCCTT GTATTACTGT TTATGTAAG                              29

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
GTGAATGGAC CAATAATAAT GACTAGAG                                          28

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CGCGCTCGTC GTATAACAGA TGCG                                              24

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TCGGTCTTAA CTGAAGCAGT TAAGC                                             25

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CGTTCAAAAT GGTATGCGTT TTGACAC                                           27

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CAGAATTGGT TAATTGGTTG TAACACTG                                          28

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

ATTTAAATGG GGGCGCTGAG GTCTGCCTCG                                        30
```

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

ATGAACGGAC CAATAATAAT GACTAGAGAA GAAAG                    35

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CGGGATCCAT TTAAATGGGG GCGCTGAGGT CTG                      33

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GCTCTAGAGG CCGGCCGGGG AAAGCCACG                          29

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

CAGTAATACA AGGGGTGTTG TGAATGGACC AATAATAATG               40

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GTTATACGAC GAGCGCGTCG GTCTTAACTG AAGCAG                 36

(2) INFORMATION FOR SEQ ID NO:18:

(i) SEQUENCE CHARACTERISTICS:
        (A) LENGTH: 38 base pairs

-continued (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CGCATACCAT TTTGAACGCA GAATTGGTTA ATTGGTTG                               38

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CAGTAATACA AGGGGTGTTA TGAACGGACC AATAATAATG                             40

(2) INFORMATION FOR SEQ ID NO:20:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CACAACGTGG CTTTCCCCGG CCCATGACCA AAATCCCTTA ACGTGAG                     47

(2) INFORMATION FOR SEQ ID NO:21:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CAGGGGGAGG TGTGGGAGGT TTTTTAAATG GGGGCGCTGA GGTCTGCC                    48